US005837763A

United States Patent [19]

Ferraro et al.

[11] Patent Number: 5,837,763

[45] Date of Patent: Nov. 17, 1998

[54] COMPOSITIONS AND METHODS FOR MANUFACTURING WAXES FILLED WITH INTERCALATES AND EXFOLIATES FORMED WITH OLIGOMERS AND POLYMERS

[75] Inventors: Robert Matthew Ferraro, Arlington Heights; Charles Randolph Landis, Lake in the Hills; Gary W. Beall, McHenry; Semeon Tsipursky, Lincolnwood; Anatoliy Sorokin, Buffalo Grove; Anatoliy Goldman, Palatine, all of Ill.

[73] Assignee: AMCOL International Corporation, Arlington Heights, Ill.

[21] Appl. No.: 582,480

[22] Filed: Jan. 3, 1996

Related U.S. Application Data

[63] Continuation-in-part of Ser. No. 525,416, Sep. 8, 1995, Pat. No. 5,721,306, which is a continuation-in-part of Ser. No. 488,264, Jun. 7, 1995, Pat. No. 5,552,469, and a continuation-in-part of Ser. No. 488,263, Jun. 7, 1995, Pat. No. 5,698,624, and a continuation-in-part of Ser. No. 480,080, Jun. 7, 1995, Pat. No. 5,578,672.

[51] Int. Cl.[6] .............................. C08J 5/10; C08K 3/34; C08L 29/00

[52] U.S. Cl. .......................... 524/449; 524/445; 524/446; 524/447; 524/448; 524/277

[58] Field of Search .................................... 524/445, 446, 524/447, 448, 449, 789, 792, 312, 376, 377, 277; 523/202, 216

[56] References Cited

U.S. PATENT DOCUMENTS

| | | | |
|---|---|---|---|
| 2,035,546 | 3/1936 | Hamilton | 167/24 |
| 3,419,460 | 12/1968 | Ure | 161/162 |
| 3,419,517 | 12/1968 | Hedrick et al. | 260/37 |
| 3,515,626 | 6/1970 | Duffield | 161/162 |
| 3,773,708 | 11/1973 | Takahashi et al. | 260/41 R |
| 3,795,650 | 3/1974 | Burns | 260/33.4 R |
| 3,912,532 | 10/1975 | Simone | 106/308 N |
| 3,929,678 | 12/1975 | Laughlin et al. | 252/526 |
| 4,125,411 | 11/1978 | Lyons | 106/291 |
| 4,210,572 | 7/1980 | Herman et al. | 260/404 |
| 4,251,576 | 2/1981 | Osborn et al. | 428/331 |
| 4,400,485 | 8/1983 | Mukamal et al. | 524/444 |
| 4,431,755 | 2/1984 | Weber et al. | 523/203 |
| 4,434,075 | 2/1984 | Mardis et al. | 252/315.2 |
| 4,472,538 | 9/1984 | Kamigaito et al. | 523/202 |
| 4,500,670 | 2/1985 | McKinley et al. | 524/445 |
| 4,546,145 | 10/1985 | Kishida et al. | 524/780 |
| 4,600,744 | 7/1986 | Libor et al. | 524/446 |
| 4,613,542 | 9/1986 | Alexander | 428/290 |
| 4,624,982 | 11/1986 | Alexander | 524/446 |
| 4,739,007 | 4/1988 | Okada et al. | 524/789 |
| 4,789,403 | 12/1988 | Rice | 106/417 |
| 4,798,766 | 1/1989 | Rice | 428/404 |
| 4,810,734 | 3/1989 | Kawasumi et al. | 523/216 |
| 4,842,651 | 6/1989 | Ravet et al. | 106/487 |
| 4,849,006 | 7/1989 | Knudson, Jr. | 71/64.11 |
| 4,889,885 | 12/1989 | Usuki et al. | 524/443 |
| 4,894,411 | 1/1990 | Okada et al. | 524/710 |
| 4,920,171 | 4/1990 | Hutton, Jr. et al. | 524/446 |
| 5,032,546 | 7/1991 | Giannelis et al. | 501/3 |
| 5,032,547 | 7/1991 | Giannelis et al. | 501/3 |
| 5,091,462 | 2/1992 | Fukui et al. | 524/504 |
| 5,102,948 | 4/1992 | Deguchi et al. | 524/789 |
| 5,164,440 | 11/1992 | Deguchi et al. | 524/444 |
| 5,164,460 | 11/1992 | Yano et al. | 624/445 |
| 5,204,078 | 4/1993 | Tateyama et al. | 423/331 |
| 5,206,284 | 4/1993 | Fukui et al. | 524/504 |
| 5,229,451 | 7/1993 | Carter et al. | 524/493 |
| 5,248,720 | 9/1993 | Deguchi et al. | 524/444 |
| 5,326,500 | 7/1994 | Friedman et al. | 252/378 |
| 5,340,558 | 8/1994 | Friedman et al. | 423/328.1 |
| 5,385,776 | 1/1995 | Maxfield et al. | 428/297 |
| 5,391,437 | 2/1995 | Miyasaka et al. | 528/425.5 |
| 5,414,042 | 5/1995 | Yasue et al. | 524/789 |
| 5,428,094 | 6/1995 | Tokoh et al. | 524/379 |
| 5,506,046 | 4/1996 | Andersen et al. | 524/446 |
| 5,508,072 | 4/1996 | Andersen et al. | 524/446 |
| 5,514,734 | 5/1996 | Maxfield et al. | 523/204 |
| 5,667,886 | 9/1997 | Gough et al. | 428/331 |

FOREIGN PATENT DOCUMENTS

| | | |
|---|---|---|
| 0 205 281 A3 | 12/1986 | European Pat. Off. . |
| 0 335 653 A1 | 10/1989 | European Pat. Off. . |
| 0 358 415 A1 | 3/1990 | European Pat. Off. . |
| 0 479 031 A1 | 8/1992 | European Pat. Off. . |
| 0 548 940 A1 | 6/1993 | European Pat. Off. . |
| 0 645 181 A2 | 3/1995 | European Pat. Off. . |
| 1 642 122 | 7/1970 | Germany . |
| 1146668 | 3/1969 | United Kingdom . |
| 1 565 362 | 4/1980 | United Kingdom . |
| WO 93/04117 | 3/1993 | WIPO . |
| WO 93/04118 | 3/1993 | WIPO . |

OTHER PUBLICATIONS

Sanchez Camazano, M. et al., "Factors influencing interactions of organophosphorus pesticides with montmorillonite", *Chemical Abstracts*, vol. 98, No. 19, 9 May 1983, Columbus, Ohio, US, Abstract No. 156367.

(List continued on next page.)

*Primary Examiner*—Vasu Jagannathan
*Assistant Examiner*—U. K. Rajguru
*Attorney, Agent, or Firm*—Marshall, O'Toole, Gerstein, Murray & Borun

[57] ABSTRACT

Compositions and methods that include a wax, in an amount of about 20% to about 99.95% by weight, containing an intercalate, or exfoliate thereof, in an amount of about 0.05% to about 80% by weight of the composition formed by contacting a layered phyllosilicate with an oligomer and/or polymer to sorb or intercalate the intercalant polymer or mixtures of intercalant polymers between adjacent phyllosilicate platelets. Sufficient intercalant polymer is sorbed between adjacent phyllosilicate platelets to expand the spacing between adjacent platelets (interlayer spacing) to a distance of at least about 5 Å, preferably to at least about 10 Å (as measured after water removal) and more preferably in the range of about 30–45 Å, so that the intercalate easily can be exfoliated, sometimes naturally, without shearing being necessary.

50 Claims, 8 Drawing Sheets

OTHER PUBLICATIONS

C. W. Francis, "Adsorption of Polyvinylpyrrolidone on Reference Clay Minerals", Soil Science, vol. 115, No. 1, 1973, pp. 40–54.

A. Usuki, et al., "Synthesis of nylon 6–clay hybrid", J. Mater. Res., vol. 8, No. 5, May 1993, pp. 1179–1184.

Y. Kojima, et al., "Mechanical Properties Of Nylon 6–Clay Hybrid", J. Mater. Res., vol. 8, No. 5, May 1993, pp. 1185–1189.

K. Suzuki, et al., "Preparation Of Delaminated Clay Having A Narrow Micropore Distribution In The Presence Of Hydroxyaluminum Cations And Polyvinyl Alcohol", Clays and Clay Minerals, vol. 36, No. 2, 1988, pp. 147–152.

R. Levy, et al., "Interlayer Adsorption of Polyvinylpyrrolidone On Montmorillonite", Journal of Colloid and Interface Science, vol. 50, No. 3, Mar. 1975, pp. 442–450.

D.J. Greeland, "Adsorption Of Polyvinyl Alcohols By Montmorillonite", Journal of Colloid Science, vol. 18, (1963) pp. 647–664.

R.A. Vaia, et al., "Synthesis and Properties of Two–Dimensional Nanostructures by Direct Intercalation of Polymer Melts in Layered Silicates", Chem. Mater. 1993, 5, pp. 1694–1696.

R.A. Vaia, et al., "New Polymer Electrolyte Nanocomposites: Melt Intercalation of Poly(ethylene oxide) in Mica–Type Silicates", Advanced Materials 1995, 7, No. 2, pp. 154–156.

A. Akelah, et al., "Synthesis and Characterization of Epoxyphilic montmorillonites", Clay Minerals (1994) 29, pp. 169–178.

C.E. Clapp, et al., "Adsorption Studies Of A Dextran On Montmorillonite", Trans. 9th Int. Cong. Soil Sci., 1968, vol. 1, pp. 627–634.

H.G.G. Dekking, "Preparation And Properties Of Some Polymer–Clay Compounds", Clays and Clay Minerals, 1964, 12, pp. 603–616.

A. Usuki, et al., "Characterization and Properties of Nylon 6—Clay Hybrid", (source and date unknown), pp. 651–652.

G.W. Brindley, et al., "Preparation And Solvation Properties Of Some Variable Charge Montmorillonites", Clays and Clay Minerals, 1971, vol. 18, pp. 399–404.

A. Okada, et al., "A Solid State NMR Study On Crystalline Forms Of Nylon 6", Journal of Applied Polymer Science, (1989), vol. 37, pp. 1363–1371.

A. Usuki, et al., Swelling Behavior Of Montmorillonite Cation Exchanged For ω–Amino Acids By ϵ–Caprolactam, J. Mater. Res., vol. 8, No. 5, May 1993, pp. 1174–1178.

Y. Kojima, et al., "One–Pot Synthesis Of Nylon 6–Clay Hybrid", Journal of Polymer Science: Part A: Polymer Chemistry, vol. 31, (1993), pp. 1755–1758.

Y. Kojima, et al., "Fine Structure Of Nylon–6–Clay Hybrid", Journal of Polymer Science: Part B: Polymer Physics, vol. 32 (1994, pp. 625–630.

B.K.G. Theng, "Clay–Polymer Interactions: Summary And Perspectives", Clays and Clay Minerals, vol. 30, No. 1 (1982) pp. 1–9.

Search Report for WO 93/04118 which was submitted with Applicants' Information Disclosure Statement dated Feb. 23, 1996, identified as B3.

Sugahara, et al., "Clay–Organic Nano–Composite; Preparation of a Kaolinite–Poly(vinylpyrrolidone) Intercalation Compound", *Journal of the Ceramic Society of Japan*, International Edition, vol. 100, No. 4, Apr. 1, 1992, pp. 420–423.

Ogawa, et al., "Preparation Of Montmorillonite–Polyacrylamide Intercalation Compounds And The Water Absorbing Property", *Clay Science*, vol. 7, 1989 Tokyo, Japan, pp. 243–251.

Wu, et al., "Structural, thermal, and electrical characterization of layered nanocomposites derived from sodium–montmorillonite and polyethers", *Chemical Abstracts*, vol. 119, No. 4, Jul. 26, 1993 Columbus, Ohio, US, Abstracts No. 31017r.

Bujdak, et al., "The reaction of montmorillonite with octadecylamine in solid and melted state", Chemical Abstracts, vol. 118, No. 26, Abstract No. 257609b, p. 166 (28 Jun. 1993), Columbus, Ohio (US).

Yano, et al., "Synthesis And Properties Of Polymide–Clay Hybrid", Polymer Preprints, ACS, Apr. 1991, pp. 65–66.

Giannelis, et al., "Synthesis And Processing Of Ceramics: Scientific Issues", Materials Research Society Symposium Proceedings, vol. 249 (1992), pp. 547–558.

FIG. 9
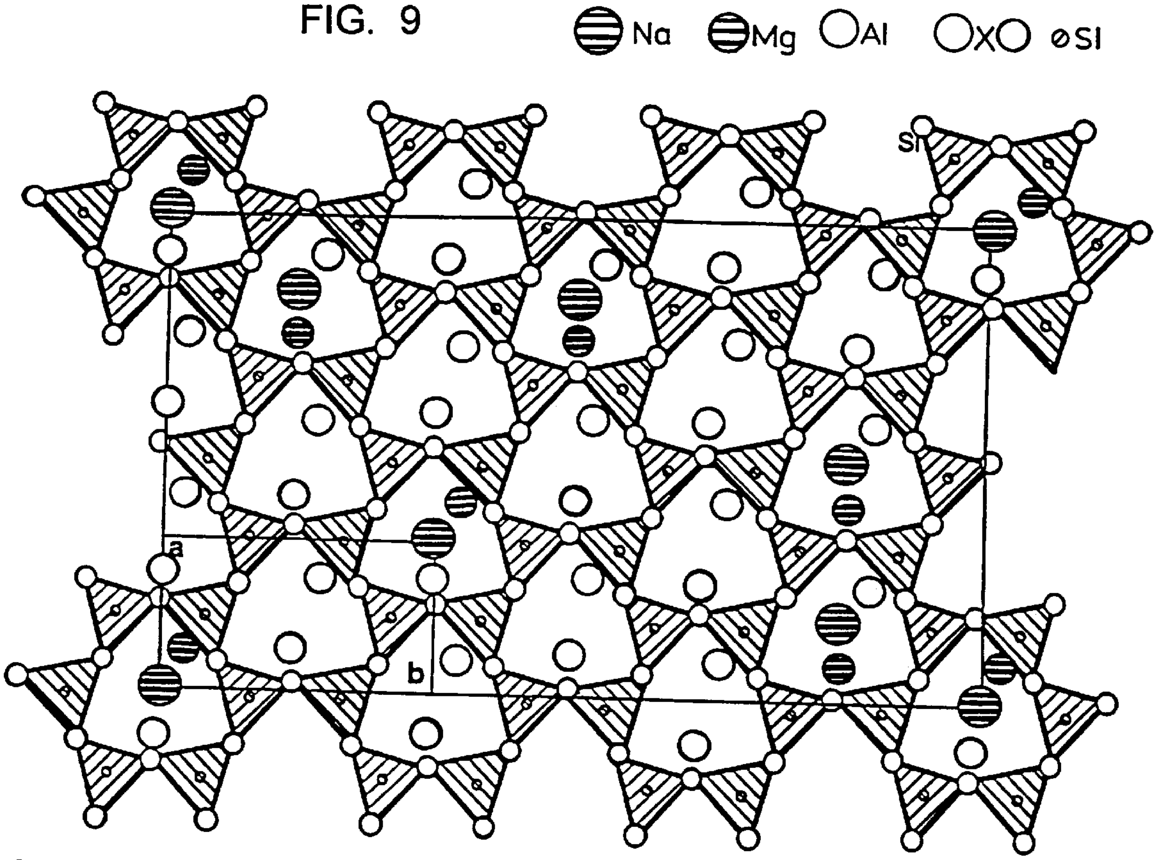
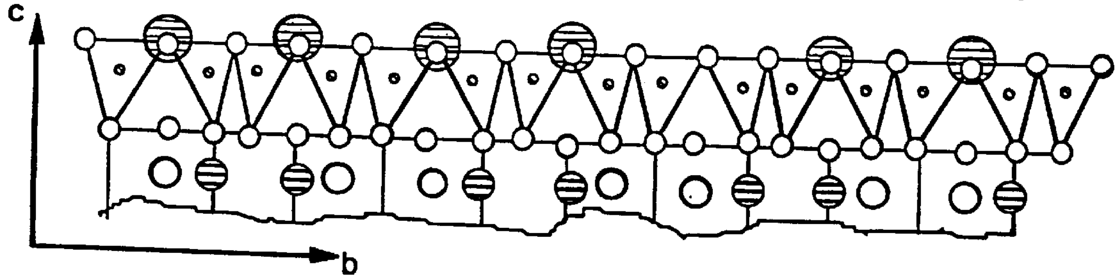
FIG. 10
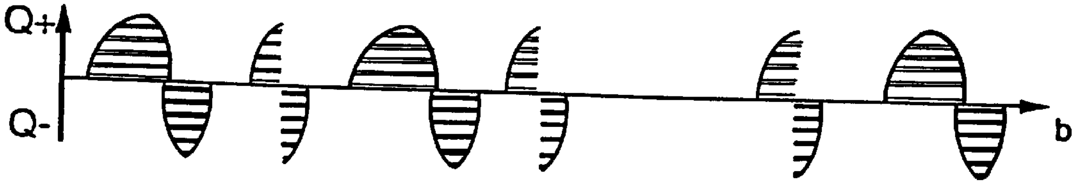
FIG. 11

COMPOSITIONS AND METHODS FOR MANUFACTURING WAXES FILLED WITH INTERCALATES AND EXFOLIATES FORMED WITH OLIGOMERS AND POLYMERS

CROSS-REFERENCE TO RELATED APPLICATIONS

This application is a continuation-in-part of application Ser. No. 08/525,416, filed Sep. 8, 1995 U.S. Pat. No. 5,721,306, which is a continuation-in-part of application Ser. No. 08/488,264 U.S. Pat. No. 5,552,469; Ser. No. 08/480,080 U.S. Pat. No. 5,578,672 and Ser. No. 08/488,263 U.S. Pat. No. 5,698,624, all filed Jun. 7, 1995.

FIELD OF THE INVENTION

The present invention is directed to waxes and wax objects filled with intercalated layered materials, and/or exfoliates thereof. The intercalates are manufactured by sorption (adsorption and/or absorption) of one or more oligomers or polymers between planar layers of a swellable layered material, such as a phyllosilicate or other layered material, to expand the interlayer spacing of adjacent layers to at least about 5 Angstroms (Å) preferably to at least about 10 Å. More particularly, the present invention is directed to compositions and methods for manufacturing candles; wax novelty items; wax paper coating compositions; paraffin waxes; chlorinated paraffin waxes; and chlorinated naphthalenes used in electrical equipment; wax sizing compositions used in textile and leather sizing; wax compositions used for waterproofing; wax polish compositions; wax fruit and vegetable coating compositions; waxes used in cosmetic and pharmaceutical creams; waxes used in carbon paper, printing ribbons and printing inks; waxes used in greases, lubricants and as mold release compositions; and the like. In accordance with the present invention, waxes useful for these industries are substantially and unexpectedly improved by incorporating into the wax about 0.05% to about 80% by weight, preferably about 0.1% to about 20% by weight, more preferably about 0.1% to about 10% by weight of one or more intercalates having at least two layers of oligomer and/or polymer molecules sorbed on the internal surfaces of adjacent layers of the planar platelets of a layered material, such as a phyllosilicate, preferably a smectite clay. The oligomer or polymer is sorbed between the platelets of the layered material to expand the interlayer spacing to at least about 5 Å, preferably to at least about 10 Å, more preferably to at least about 20 Å, and most preferably to at least about 30–45 Å, up to about 100 Å, or disappearance of periodicity. The resulting intercalates are neither entirely organophilic nor entirely hydrophilic, but a combination of the two, and easily can be exfoliated for or during admixture with any wax material, to improve one or more properties of the wax, particularly to reduce shrinkage and cracking when the wax is melted and cooled for solidification into a desired shape. The resulting compositions comprising a wax and an intercalate and/or an exfoliate thereof are useful wherever wax compositions are used, for example, as candles, shaped wax novelty items, in electrical equipment, coating compositions and the like, to decrease shrinkage of the wax, increase elasticity and temperature characteristics, such as melting point; and increase the stability (reduction in separation of components upon standing and solidification) of the wax composition. Other advantages include increasing the opacity and dye receptivity and an increase in wax melt viscosity for wick flame control in candles; increasing composition hardness without causing brittleness; improving the melt stability of the composition to make sure that the liquid composition remains homogenous, without component separation; reducing or eliminating the need for purer, more expensive wax components, such as microcrystalline wax; and greatly reducing or eliminating the formation of exterior bubbles or pock marks that form upon reheating an upper portion of a candle when reducing the concave upper candle end formed upon initial solidification; and providing the capability of eliminating typical opacifying agents and viscosity increasing agents, e.g. ethylene vinylacetate copolymers, fatty acids, such as stearic acid, and the like, with a much lower amount of the nanoscale platelet particles of the present invention. Additionally, the phyllosilicate platelets act as a good protector against deterioration of physical properties and color degradation caused by ultraviolet (UV) light so that UV protectors are unnecessary in the wax compositions of the present invention.

BACKGROUND OF THE INVENTION AND PRIOR ART

It is well known that phyllosilicates, such as smectite clays, e.g., sodium montmorillonite and calcium montmorillonite, can be treated with organic molecules, such as organic ammonium ions, to intercalate the organic molecules between adjacent, planar silicate layers, thereby substantially increasing the interlayer (interlaminar) spacing between the adjacent silicate layers. The thus-treated, intercalated phyllosilicates, having interlayer spacing of at least about 10–20 Å and up to about 100 Å, then can be exfoliated, e.g., the silicate layers are separated, e.g., mechanically, by high shear mixing. The individual silicate layers, when admixed with a matrix polymer, before, after or during the polymerization of the matrix polymer, e.g., a polyamide—see U.S. Pat. Nos. 4,739,007; 4,810,734; and 5,385,776—have been found to substantially improve one or more properties of the polymer, such as mechanical strength and/or high temperature characteristics.

Exemplary of such prior art composites, also called "nanocomposites", are disclosed in published PCT disclosure of Allied Signal, Inc. WO 93/04118 and U.S. Pat. No. 5,385,776, disclosing the admixture of individual platelet particles derived from intercalated layered silicate materials, with a polymer to form a polymer matrix having one or more properties of the matrix polymer improved by the addition of the exfoliated intercalate. As disclosed in WO 93/04118, the intercalate is formed (the interlayer spacing between adjacent silicate platelets is increased) by adsorption of a silane coupling agent or an onium cation, such as a quaternary ammonium compound, having a reactive group which is compatible with the matrix polymer. Such quaternary ammonium cations are well known to convert a highly hydrophilic clay, such as sodium or calcium montmorillonite, into an organophilic clay capable of sorbing organic molecules. A publication that discloses direct intercalation (without solvent) of polystyrene and poly (ethylene oxide) in organically modified silicates is *Synthesis and Properties of Two-Dimensional Nanostructures by Direct Intercalation of Polymer Melts in Layered Silicates*, Richard A. Vaia, et al., *Chem. Mater.,* 5:1694–1696(1993). Also as disclosed in *Adv. Materials,* 7, *No.* 2: (1985), pp, 154–156, *New Polymer Electrolyte Nanocomposites: Melt Intercalation of Poly(Ethylene Oxide) in Mica-Type Silicates*, Richard A. Vaia, et al., poly(ethylene oxide) can be intercalated directly into Na-montmorillonite and Li-montmorillonite by heating to 80° C. for 2–6 hours to achieve a d-spacing of 17.7 Å. The intercalation is accompanied by displacing water molecules, disposed between the clay platelets with polymer molecules. Apparently, however, the intercalated material could not be exfoliated and was tested in pellet form. It was quite surprising to one of the authors of these articles that exfoliated material could be manufactured in accordance with the present invention.

Previous attempts have been made to intercalate polyvinylpyrrolidone (PVP), polyvinyl alcohol (PVA) and poly (ethylene oxide) (PEO) between montmorillonite clay platelets with little success. As described in Levy, et al., *Interlayer Adsorption of Polyvinylpyrrolidone on Montmorillonite*, Journal of Colloid and Interface Science, Vol. 50, No. 3, March 1975, pages 442–450, attempts were made to sorb PVP (40,000 average M.W.) between monoionic montmorillonite clay platelets (Na, K, Ca and Mg) by successive washes with absolute ethanol, and then attempting to sorb the PVP by contact with 1% PVP/ethanol/water solutions, with varying amounts of water, via replacing the ethanol solvent molecules that were sorbed in washing (to expand the platelets to about 17.7 Å). Only the sodium montmorillonite had expanded beyond a 20 Å basal spacing (e.g., 26 Å and 32 Å), at $5^{+}$% $H_2O$, after contact with the PVP/ethanol/$H_2O$ solution. It was concluded that the ethanol was needed to initially increase the basal spacing for later sorption of PVP, and that water did not directly affect the sorption of PVP between the clay platelets (Table II, page 445), except for sodium montmorillonite. The sorption was time consuming and difficult and met with little success.

Further, as described in Greenland, *Adsorption of Polyvinyl Alcohols by Montmorillonite*, Journal of Colloid Sciences, Vol. 18, pages 647–664 (1963), polyvinyl alcohols containing 12% residual acetyl groups could increase the basal spacing by only about 10 Å due to the sorbed polyvinyl alcohol (PVOH). As the concentration of polymer in the intercalant polymer-containing solution was increased from 0.25% to 4%, the amount of polymer sorbed was substantially reduced, indicating that sorption might only be effective at polymer concentrations in the intercalant polymer-containing composition on the order of 1% by weight polymer, or less. Such a dilute process for intercalation of polymer into layered materials would be exceptionally costly in drying the intercalated layered materials for separation of intercalate from the polymer carrier, e.g., water, and, therefore, apparently no further work was accomplished toward commercialization.

In accordance with one embodiment of the present invention, intercalates are prepared by contacting a phyllosilicate with a PVP polymer, preferably essentially alcohol-free, or a PVA intercalant polymer composition, wherein the PVA preferably contains 5% or less residual acetyl groups, more preferably fully hydrolyzed, containing 1% or less acetyl groups.

In accordance with an important feature of the present invention, best results are achieved using an oligomer (herein defined as a pre-polymer having 2 to about 15 recurring monomeric units, which can be the same or different) or polymer (herein defined as having more than about 15 recurring monomeric units, which can be the same or different) composition for intercalation having at least about 2%, preferably at least about 5% by weight intercalant oligomer or intercalant polymer concentration, more preferably about 30% to about 80% by weight oligomer and/or polymer, based on the weight of oligomer and/or polymer and carrier (e.g., water with or without another solvent for the intercalant oligomer or intercalant polymer) to achieve better sorption of the intercalant polymers between phyllosilicate platelets. Regardless of the concentration of intercalant polymer in liquid carrier of the intercalating composition, the intercalating composition should have a polymer:layered material weight ratio of at least about 1:20, preferably at least about 1:10, more preferably at least about 1:5, and most preferably about 1:4 to achieve efficient intercalation of the polymer between adjacent platelets of the layered material. The oligomer or polymer sorbed between and permanently bonded to the silicate platelets causes separation or added spacing between adjacent silicate platelets and, for simplicity of description, both the oligomers and polymers are hereinafter called the "intercalant" or "intercalant polymer" or "polymer intercalant". In this manner, the water-soluble oligomers or polymers will be sorbed sufficiently to increase the interlayer spacing of the phyllosilicate in the range of about 10 Å to about 100 Å, for easier and more complete exfoliation, in a commercially viable process, regardless of the particular phyllosilicate or intercalant polymer.

In accordance with the present invention, it has been found that a layered material, such as a phyllosilicate, e.g., a smectite clay, can be intercalated sufficiently for subsequent exfoliation by sorption of polymers or oligomers that have functionalities, or aromatic rings to provide bonding of the polymer or oligomer to the internal surfaces of the layered material by a mechanism selected from the group consisting of ionic complexing; electrostatic complexing; chelation; hydrogen bonding; dipole/dipole; Van Der Waals forces; and any combination thereof. Such bonding is between two functional groups of one or two intercalant polymer molecules and the metal cations bonded to the inner surfaces of the phyllosilicate platelets. Sorption and metal cation electrostatic attraction or bonding of a platelet metal cation between two functional groups of the intercalant polymer molecules; or the electrostatic bonding between the interlayer cations in hexagonal or pseudohexagonal rings of the smectite layers and an intercalant polymer aromatic ring structure increases the interlayer spacing between adjacent silicate platelets or other layered material to at least about 5 Å, preferably at least about 10 Å, more preferably at least about 20 Å, and most preferably in the range of about 30 Å to about 45 Å. Such intercalated phyllosilicates easily can be exfoliated into individual phyllosilicate platelets before or during admixture with a wax material to form a wax/platelet composite material, or nanocomposite, having one or more of the wax properties substantially improved in comparison with the wax alone.

DEFINITIONS

Whenever used in this Specification, the terms set forth shall have the following meanings:

"Layered Material" shall mean an inorganic material, such as a smectite clay mineral, that is in the form of a plurality of adjacent, bound layers and has a maximum thickness, for each layer, of about 3 Å to about 50 Å, preferably about 10 Å.

"Platelets" shall mean individual layers of the Layered Material.

"Intercalate" or "Intercalated" shall mean a Layered Material that includes oligomer and/or polymer molecules disposed between adjacent platelets of the Layered Material to increase the interlayer spacing between the adjacent platelets to at least about 5 Å, preferably to at least about 10 Å.

"Intercalation" shall mean a process for forming an Intercalate.

"Intercalant Polymer" or "Intercalant" shall mean an oligomer or polymer that is sorbed between Platelets of the Layered Material to form an Intercalate.

"Intercalating Carrier" shall mean a carrier comprising water with or without an organic solvent used together with an Intercalant Polymer to form an Intercalating Composition capable of achieving Intercalation of the Layered Material.

"Intercalating Composition" shall mean a composition comprising an Intercalant, an Intercalating Carrier for the Intercalant, and a Layered Material.

"Exfoliate" or "Exfoliated" shall mean individual platelets of an Intercalated Layered Material so that adjacent platelets of the Intercalated Layered Material can be dispersed individually throughout a wax carrier material, such as paraffin wax used to form a candle.

"Exfoliation" shall mean a process for forming an Exfoliate from an Intercalate.

SUMMARY OF THE INVENTION

In brief, the present invention is directed to compositions and methods that include a wax, in an amount of about 20% to about 99.95% by weight, containing an intercalate, or exfoliate thereof, in an amount of about 0.05% to about 80% by weight of the composition formed by contacting a layered phyllosilicate with an oligomer and/or polymer to sorb or intercalate the intercalant polymer or mixtures of intercalant polymers between adjacent phyllosilicate platelets. Sufficient intercalant polymer is sorbed between adjacent phyllosilicate platelets to expand the spacing between adjacent platelets (interlayer spacing) to a distance of at least about 5 Å, preferably to at least about 10 Å (as measured after water removal) and more preferably in the range of about 30–45 Å, so that the intercalate easily can be exfoliated, sometimes naturally, without shearing being necessary. At times, the intercalate requires shearing that easily can be accomplished, e.g., when mixing the intercalate with the wax, either by extrusion, or by mixing with a wax melt, to provide a wax/platelet composite material or nanocomposite—the platelets being obtained by exfoliation of the intercalated phyllosilicate.

The intercalant polymer should have an affinity for the phyllosilicate so that it is sorbed between, and is maintained associated with the silicate platelets in the interlayer spaces, and after exfoliation. In accordance with the present invention, the intercalant polymer can be water-soluble, water dispersible, or water-insoluble, so long as the polymer includes a functionality selected from the group consisting of carbonyl, hydroxyl, carboxyl, amine, amide, ether, ester, sulfate, sulfonate, sulfinate, sulfamate, phosphate, phosphonate, and/or phosphinate. Preferably, the intercalant polymer should be sufficiently water-soluble (herein defined as sufficiently soluble such that at least 0.1 gram of the polymer will dissolve per 100 grams of distilled water at 25° C.). In accordance with the present invention, the intercalant polymer should include an aromatic ring and/or have a functionality selected from the group consisting of a carbonyl; carboxyl; hydroxyl; amine; amide; ether; ester; sulfate; sulfonate; sulfinate; sulfamate; phosphate; phosphonate; and/or phosphinate structures to be sufficiently bound by a mechanism selected from the group consisting of ionic complexing; electrostatic complexing; chelation; hydrogen bonding; dipole/dipole; Van Der Waals forces; and any combination thereof. Such bonding results from the metal cations of the phyllosilicate, bonded to the inner surfaces of the phyllosilicate platelets, sharing electrons with two functional groups of one or two intercalant polymer molecules. Such intercalant polymers have sufficient affinity for the phyllosilicate platelets to maintain sufficient interlayer spacing for exfoliation, without the need for coupling agents or spacing agents, such as the onium ion or silane coupling agents disclosed in the above-mentioned prior art.

Sorption of the intercalant polymer should be sufficient to achieve expansion of adjacent platelets of the layered material (when measured dry) to an interlayer spacing of at least about 5 Å, preferably at least about 10 Å, more preferably a spacing of at least about 20 Å, and most preferably a spacing of about 30–45 Å. To achieve intercalates that can be exfoliated easily using the water-soluble polymer intercalants disclosed herein, such as polyvinylpyrrolidone, polyvinyl alcohol, and mixtures thereof, the weight ratio of intercalant polymer to layered material in the intercalating composition contacting the phyllosilicate should be at least about 1:20, preferably at least about 1:10, more preferably at least about 1:5, and most preferably about 1:5 to 1:3. It is preferred that the concentration of intercalant polymer in the intercalating composition, based on the total weight of intercalant polymer plus intercalant carrier in the intercalating composition, is at least about 15% by weight, more preferably at least about 20% by weight intercalant polymer, for example about 20–30% to about 90% by weight intercalant polymer, based on the weight of intercalant polymer plus intercalant carrier in the intercalant composition during intercalation.

It has been found that the intercalates of the present invention are increased in interlayer spacing step-wise. If the phyllosilicate is contacted with an intercalant polymer-containing composition containing less than about 16% by weight polymer, e.g., 10% to about 15% by weight polymer, based on the dry weight of the phyllosilicate, a monolayer width of polymer is sorbed (intercalated) between the adjacent platelets of the layered material. A monolayer of polymer intercalated between platelets increases the interlayer spacing to a distance in the range of about 5 Å to less than about 10 Å. When the amount of intercalant polymer is in the range of about 16% to less than about 35% by weight, based on the weight of the dry layered material, the intercalant polymer is sorbed in a bilayer, thereby increasing the interlayer spacing to a distance in the range of about 10 Å to about 16 Å. At an intercalant polymer loading in the intercalating composition of about 35% to less than about 55% intercalant polymer, based on the dry weight of the layered material contacted, the interlayer spacing is increased to a distance in the range of about 20 Å to about 25 Å, corresponding to three layers of intercalant polymer sorbed between adjacent platelets of the layered material. At an intercalant polymer loading of about 55% to about 80% intercalant polymer, based on the dry weight of the layered material in the intercalating composition, the interlayer spacing will be increased to a distance in the range of about 30 Å to about 35 Å, corresponding to 4 and 5 layers of intercalant polymer sorbed (intercalated) between adjacent platelets of the layered material.

Such interlayer spacings have never been achieved by direct intercalation of an oligomer or polymer molecule, without prior sorption of a swelling agent, such as an onium or silane coupling agent, and provides easier and more complete exfoliation for or during incorporation of the platelets into a thermoplastic or thermosetting matrix polymer. Such intercalates are especially useful in admixture with matrix thermoplastic or thermosetting polymers in the manufacture of polymeric articles from the polymer/platelet composite materials; and for admixture of the intercalates and exfoliated intercalates with polar solvents in modifying rheology, e.g., of cosmetics, oil-well drilling fluids, in the manufacture of oil and grease, and the like.

Once exfoliated, the platelets of the intercalate are predominantly completely separated into individual platelets and the originally adjacent platelets no longer are retained in a parallel, spaced disposition, but are free to move as predominantly individual platelets throughout a matrix polymer melt to act similar to a nanoscale filler material for the matrix polymer. Once the polymer/platelet composite material is set and hardened into a desired shape, the predominantly individual phyllosilicate platelets are permanently fixed in position and are randomly, homogeneously and uniformly dispersed, predominantly as individual platelets, throughout the matrix polymer/platelet composite material.

As recognized, the thickness of the exfoliated, individual platelets (about 10 Å) is relatively small compared to the size of the flat opposite platelet faces. The platelets have an aspect ratio in the range of about 200 to about 2,000. Dispersing such finely divided platelet particles into a wax composition provides a very large area of contact between wax and platelet particles, for a given volume of particles in the composite, and a high degree of platelet homogeneity in the composite material.

BRIEF DESCRIPTION OF THE DRAWINGS

FIG. 9 is a schematic representation of a top view of sodium montmorillonite clay showing the ionic charge distribution for the sodium montmorillonite clay top and interlayer surfaces showing $Na^+$ ions as the largest circles as well as magnesium and aluminum ions and Si and oxygen (Ox) atoms disposed beneath the sodium ions;

FIG. 10 is a side view (bc-projection) of the schematic representation of FIG. 6; and FIG. 11 is a schematic representation of the charge distribution on the surfaces of sodium montmorillonite clay platelets showing the distribution of positive and negative charges on the clay platelet surfaces as a result of the natural disposition of the Na, Mg, Al, Si, and oxygen (Ox) atoms of the clay shown in FIGS. 6 and 7.

DETAILED DESCRIPTION OF THE PREFERRED EMBODIMENTS

Figure 1:
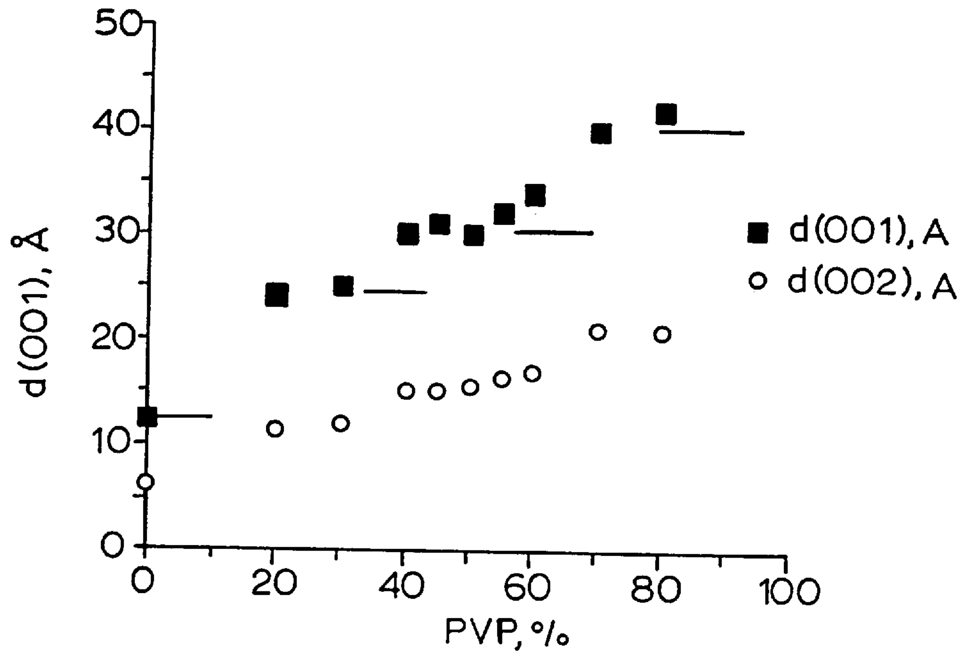
FIG. 1 is a graph plotting interlayer space for polyvinylpyrrolidone (PVP):smectite clay complexes (intercalates) showing d(001) and d(002) spacing, in Angstroms, between smectite clay platelets versus percentage of PVP sorbed, based on the dry weight of the smectite clay.

To form the intercalated materials useful in admixture with one or more waxes in accordance with the present invention, the phyllosilicate should be swelled or intercalated by sorption of an oligomer or polymer that includes an aromatic ring and/or a functionality selected from the group consisting of carbonyl; carboxyl; hydroxyl; amine; amide; ether; ester, sulfate, sulfonate, sulfinate, sulfamate, phosphate, phosphonate, phosphinate, or combinations thereof. In accordance with a preferred embodiment of the present invention, the intercalating composition should include at least about 4% by weight water, up to about 5000% by weight water, based on the dry weight of the phyllosilicate, preferably about 7% to about 100% water, more preferably about 25% to about 50% by weight water, prior to or during contact with the intercalant polymer to achieve sufficient intercalation for exfoliation. Preferably, the phyllosilicate should include at least about 4% by weight water before contact with the intercalating carrier for efficient intercalation. The amount of intercalant polymer in contact with the phyllosilicate from the intercalating composition, for efficient exfoliation, should provide an intercalant polymer/phyllosilicate weight ratio (based on the dry weight of the phyllosilicate) of at least about 1:20, preferably at least about 3.2:20, and more preferably about 4–14:20, to provide efficient sorption and complexing (intercalation) of the polymer between the platelets of the layered material, e.g., phyllosilicate, (preferably about 16 to about 70 percent by weight intercalant polymer, based on the dry weight of the layered silicate material).

The preferred polymer intercalants are water-soluble and are added to the intercalating composition in the form of a solid or liquid (neat or aqueous solution or dispersion, with or without a liquid organic solvent, e.g., alcohol) having an intercalant polymer concentration of at least about 2%, preferably at least about 5% by weight polymer, more preferably at least about 50% to about 100% by weight intercalant polymer in the intercalating composition, based on the dry weight of the layered material, for intercalant polymer sorption. The polymer can be added as a solid with the addition to the layered material/polymer blend of at least about 20% water, preferably at least about 30% water to about 5000% water or more, based on the dry weight of the layered material, with or without another solvent for the intercalant polymer. Preferably about 30% to about 50% water, more preferably about 30% to about 40% by weight water, based on the dry weight of the layered material, is included in the intercalating composition, when extruding or pug milling, so that less water or solvent is sorbed by the intercalate, thereby necessitating less drying energy after intercalation. The intercalant polymer may be introduced into the spaces between every layer, nearly every layer, or at least a predominance of the layers of the layered material such that the subsequently exfoliated platelet particles are preferably, predominantly less than about 5 layers in thickness; more preferably, predominantly about 1 or 2 layers in thickness; and most preferably, predominantly single platelets.

Any swellable layered material that sufficiently sorbs the intercalant polymer to increase the interlayer spacing between adjacent phyllosilicate platelets to at least about 5 Å, preferably at least about 10 Å (when the phyllosilicate spacing is measured dry—having a maximum of about 5% by weight water) may be used in the practice of this invention. Useful swellable layered materials include phyllosilicates, such as smectite clay minerals, e.g., montmorillonite, particularly sodium montmorillonite; magnesium montmorillonite and/or calcium montmorillonite; nontronite; beidellite; volkonskoite; hectorite; saponite; sauconite; sobockite; stevensite; svinfordite; vermiculite; and the like. Other useful layered materials include micaceous minerals, such as illite and mixed layered illite/smectite minerals, such as rectorite, tarosovite, ledikite and admixtures of illites with the clay minerals named above.

Other layered materials having little or no charge on the layers may be useful in this invention provided they can be intercalated with the intercalant polymers to expand their interlayer spacing to at least about 5 Å, preferably to at least about 10 Å. Preferred swellable layered materials are phyllosilicates of the 2:1 type having a negative charge on the layers ranging from about 0.15 to about 0.9 charges per formula unit and a commensurate number of exchangeable metal cations in the interlayer spaces. Most preferred layered materials are smectite clay minerals such as montmorillonite, nontronite, beidellite, volkonskoite, hectorite, saponite, sauconite, sobockite, stevensite, and svinfordite.

As used herein the "interlayer spacing" refers to the distance between the internal faces of the adjacent dry layers as they are assembled in the layered material before any delamination (exfoliation) takes place. The interlayer spacing is measured when the layered material is "air dry", e.g., contains about 3–10% water, preferably about 3–6% by weight water, based on the dry weight of the layered material. The preferred clay materials generally include interlayer cations such as $Na^+$, $Ca^{+2}$, $K^+$, $Mg^{+2}$, $NH_4^+$ and the like, including mixtures thereof.

The amount of intercalant polymer intercalated into the swellable layered materials useful in this invention, in order that the intercalated layered material platelet surfaces sufficiently complex with the polymer molecules, such that the layered material may be easily exfoliated or delaminated into individual platelets, may vary substantially between about 10% and about 80%, based on the dry weight of the layered silicate material. In the preferred embodiments of the invention, amounts of polymer intercalants employed, with respect to the dry weight of layered material being intercalated, will preferably range from about 8 grams of intercalant polymer/100 grams of layered material (dry basis), preferably at least about 10 grams of polymer/100 grams of layered material to about 80–90 grams intercalant polymer/100 grams of layered material. More preferred amounts are from about 20 grams intercalant polymer/100 grams of layered material to about 60 grams intercalant polymer/100 grams of layered material (dry basis).

The polymer intercalants are introduced into (sorbed within) the interlayer spaces of the layered material in one of two ways. In a preferred method of intercalating, the layered material is intimately mixed, e.g., by extrusion or pug milling, to form an intercalating composition comprising the layered material, in an intercalant polymer or intercalant polymer/water solution, or intercalant polymer, water and an organic solvent. To achieve sufficient intercalation for exfoliation, the layered material/intercalant polymer blend contains at least about 8% by weight, preferably at least about 10% by weight intercalant polymer, based on the dry weight of the layered material. The intercalating carrier (preferably water, with or without an organic solvent) can be added by first solubilizing or dispersing the intercalant polymer in the carrier; or the dry intercalant polymer and relatively dry phyllosilicate (preferably containing at least about 4% by weight water) can be blended and the intercalating carrier added to the blend, or to the phyllosilicate prior to adding the dry intercalant polymer. In every case, it has been found that surprising sorption and complexing of intercalant polymer between platelets is achieved at relatively low loadings of intercalating carrier, especially $H_2O$, e.g., at least about 4% by weight water, based on the dry weight of the phyllosilicate. When intercalating the phyllosilicate in slurry form (e.g. 900 pounds water, 100 pounds phyllosillicate, 25 pounds polymer) the amount of water can vary from a preferred minimum of at least about 30% by weight water, with no upper limit to the amount of water in intercalating composition (the phyllosilicate intercalate is easily separated from the intercalating composition).

Alternatively, the intercalating carrier, e.g., water, with or without an organic solvent, can be added directly to the phyllosilicate prior to adding the intercalant polymer, either dry or in solution. Sorption of the polymer intercalant molecules may be performed by exposing the layered material to dry or liquid polymer intercalant compositions containing at least about 2% by weight, preferably at least about 5% by weight intercalant polymer, more preferably at least about 50% intercalant polymer, based on the dry weight of the layered material. Sorption may be aided by exposure of the intercalating composition to heat, pressure, ultrasonic cavitation, or microwaves.

In accordance with another method of intercalating the intercalant polymer between the platelets of the layered material and exfoliating the intercalate, the layered material, containing at least about 4% by weight water, preferably about 10% to about 15% by weight water, is blended with an aqueous solution of a water-soluble intercalant polymer in a ratio sufficient to provide at least about 8% by weight, preferably at least about 10% by weight intercalant polymer, based on the dry weight of the layered material. The blend then preferably is extruded for faster intercalation of the polymer with the layered material.

The preferred polymer intercalants are water-soluble, such as polyvinylpyrrolidone (PVP) having a monomeric structure (I) as follows:

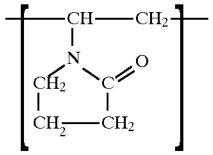

(I)

The water-solubility of PVP can be adjusted according to (1) the degree of hydrolysis of the polyvinyl-pyrrolidone, and (2) by forming a metal salt of PVP, such as sodium or potassium. PVP can be hydrolyzed to the structure (II):

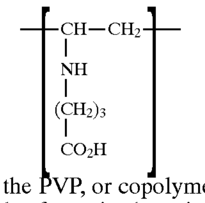

(II)

and the PVP, or copolymers of vinylpyrrolidone and a vinyl amide of γ-amine butyric acid, can be intercalated in the salt form, e.g., sodium or potassium polyvinylpyrrolidone polymers. Preferred PVP intercalants, and the following PVP derivatives, should have a weight average molecular weight in the range of about 100 to about 100,000 or more, more preferably about 1,000 to about 40,000.

Other suitable water-soluble vinyl polymers include poly (vinyl alcohol)

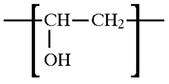

The polyvinyl alcohols function best when they are essentially fully hydrolyzed, e.g., 5% or less acetyl groups, preferably 1% or less residual acetyl groups. The lower molecular weight PVA's function best, e.g., a weight average molecular weight of about 2,000 to about 10,000, but higher molecular weights also function, e.g., up to about 100,000.

The polyacrylic acid polymers and copolymers and partially or fully neutralized salts, e.g., metal salts, are also suitable, having monomer units:

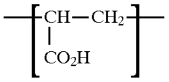

and are commercially available as CARBOPOL resins from B. F. Goodrich and PRIMAL resins from Rohm & Haas. Light cross-linking is acceptable, so long as water-solubility is retained. Weight average molecular weights, for the polyacrylic polymers and copolymers described above and below, of about 10,000 or less, e.g., 200–10,000, intercalate more easily, but higher molecular weights up to about 100,000 or more also function.

Other water-soluble derivatives of, and substituted, polyacrylic acids also are useful as intercalant polymers in accordance with the present invention, such as poly (methacrylic acid), (PMAA), having a monomeric structure:

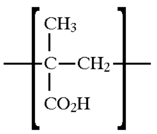

Similar water-soluble polymers and copolymers that are suitable in accordance with the present invention include poly(methacrylamide), or PMAAm, having a general monomeric structure:

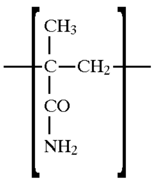

Poly(N,N-Dimethylacrylamide), having the general monomeric structure:

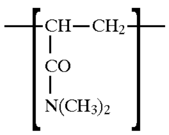

Poly(N-Isopropylacrylamide), or PIPAAm, having the monomeric structure:

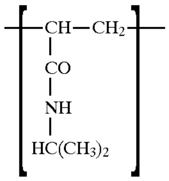

Poly(N-acetamidoacrylamide), having a monomeric structure:

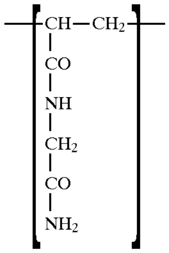

and Poly(N-acetmidomethacrylamide), having a monomeric structure:

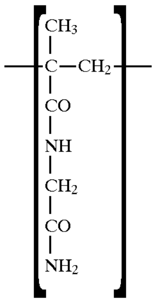

Water-soluble copolymers including any one or more of the above-described acrylic polymers also are useful in accordance with the principles of the present invention, including the acrylic interpolymers of polyacrylic acid and poly (methacrylic acid); polyacrylic acid with poly (methacrylamide); and polyacrylic acid with methacrylic acid.

Other suitable water-soluble polymers include polyvinyloxazolidone (PVO) and polyvinylmethyloxazolidone (PVMO), having the monomeric structures:

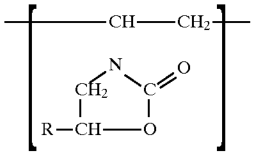

PVO: R = H
PVMO: R = $CH_3$

Also suitable are polyoxypropylene, polyoxyethylene block polymers that conform to the formulas:

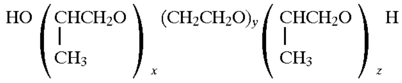

and

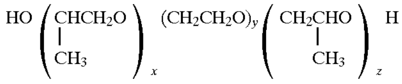

wherein x and z are each an integer in the range of about 4 to about 30; and y is an integer in the range of about 4 to about 100, for example Meroxapol 105; Meroxapol 108; Meroxapol 171; Meroxapol 172; Meroxapol 174; Meroxapol 178; Meroxapol 251; Meroxapol 252; Meroxapol 254; Meroxapol 255; Meroxapol 258; Meroxapol 311; Meroxapol 312; and Meroxapol 314.

Other suitable water-soluble/water-dispersible intercalant polymers include polyacrylamide and copolymers of acrylamide; acrylamide/sodium acrylate copolymer; acrylate/acrylamide copolymer; acrylate/ammonium methacrylate copolymer; acrylate/diacetoneacrylamide copolymers; acrylic/acrylate copolymers; adipic acid/dimethylaminohydroxypropyl diethylenetriamine copolymer; ammonium acrylate copolymers; ammonium styrene/acrylate copolymers; ammonium vinyl acetate/acrylate copolymers; AMP acrylate/diacetoneacrylamide copolymers; AMPD acrylate/diacetoneacrylamide copolymers; butyl benzoic acid/phthalic anhydride/trimethylolethane copolymer; cornstarch/acrylamide/sodium acrylate copolymer; diethylene glycolamine/epichlorohydrin/piperazine copolymer; dodecanedioic acid/cetearyl alcohol/glycol copolymers; ethylene/vinyl alcohol copolymer; ethyl ester of polyethyleneimines, such as hydroxyethyl/PEI-1000 and hydroxyethyl PEI-1500; isopropyl ester of PVM/MA copolymer; melamine/formaldehyde resin; methacryloyl ethyl betaine/methacrylate copolymers; methoxy PEG-22/dodecyl glycol copolymer; octadecene/maleic anhydride copolymer; octylacrylamide/acrylate/butylaminoethyl methacrylate copolymers; octylacrylamide/acrylate copolymers; PEG/dodecyl glycol copolymers; polyethyleneimines, such as PEI-7; PEI-15; PEI-30; PEI-45; PEI-275; PEI-700; PEI-1000; PEI-1500; and PEI-2500; phthalic anhydride/glycerin/glycidyl decanoate copolymer; metal salts of acrylic and polyacrylic acid; polyaminopropyl biguanide; polymeric quaternary ammonium salts, such as polyquaternium-1; polyquaternium-2; polyquaternium-4; polyquaternium-5; polyquaternium-6; polyquaternium-7; polyquaternium-8; polyquaternium-9; polyquaternium-10; polyquaternium-11; polyquaternium-12; polyquaternium-13; polyquaternium-14; and polyquaternium-15; polyvinyl imidazolinium acetate; potassium polyacrylate; sodium polyacrylate; metal salts of PVM/MA copolymers, e.g. Li, K, Na, Ru, Ce salts; PVP/eicosene copolymers; PVP/ethyl methacrylate/methacrylic acid copolymer; PVP/hexadecene copolymer; PVP/VA copolymer; PVP/vinyl acetate/itaconic acid copolymer; sodium acrylate/vinyl alcohol copolymers; sodium $C_4$–$C_{12}$, and other metal salts of olefin/maleic acid copolymers; sodium polymethacrylate; sodium polystyrene sulfonate; sodium styrene/acrylate/PEG-10 dimaleate copolymer; water-soluble esters and ethers of cellulose; sodium styrene/PEG-10 maleate/nonoxynol-10 maleate/acrylate copolymer; starch/acrylate/acrylamide copolymers; styrene/acrylamide copolymer; styrene/acrylate/ammonium methacrylate copolymer; styrene/maleic anhydride copolymer; styrene/PVO copolymer; sucrose benzoate/sucrose acetate isobutyrate/butyl benzyl phthalate copolymer; sucrose benzoate/sucrose acetate isobutyrate/butyl benzylphthalate/methyl methacrylate copolymer; urea/formaldehyde prepolymers; urea/melamine/formaldehyde prepolymers; vinyl acetate/crotonic acid copolymers; and vinyl alcohol copolymers.

Other water-soluble polymeric polyols and polyhydric alcohols, such as polysaccharides, also are suitable as polymer intercalants.

Any wax is useful in the compositions of the present invention. The useful waxes may be natural or synthetic, or combinations thereof, and generally have melting points within the range of about 30° C. to about 100° C., including animal waxes, mineral waxes, vegetable waxes, insect waxes, and synthetic waxes including: beeswax; bayberry-myrtle; candelilla; caranday; carnauba; castor bean wax; esparto grass wax; Japan wax; montan crude wax; ouricury; retamo-ceri nimbi; shellac wax; spermaceti; sugar cane wax; and wool wax-lanolin.

Of these waxes, the petroleum waxes and synthetic waxes are preferred for the compositions of the present invention. Synthetic waxes include the ester waxes made by esterifying acid waxes, such as montan wax, with alcohols and/or glycols. Paraffins and chlorinated paraffins also are of considerable interest as the wax components of the compositions of the present invention. Waxy film formers produced by the emulsion polymerization of ethylene, styrene, or acrylates (weight average molecular weights of about 10,000 to about 50,000) are of particular interest in the compositions of the present invention in the manufacture of polyolefin films, filled with intercalates and/or exfoliates, having increased gas impermeability. Oxidized hydrocarbon waxes, such as those manufactured from the Fisher-Tropsch paraffins, and the microcrystalline petroleum waxes (ester-type waxes) also are useful in the compositions of the present invention, particularly for polishes and the like.

Other synthetic waxes of entirely different structure such as the fatty amides, imides, amines, and nitrites can be waxlike and very useful, particularly when special surface activity or coordinate solubilities are needed. The polyoxyethylenes or carbowaxes are a unique and important group of waxes because of their water solubility and compatibility with fatty materials common to cosmetic and pharmaceutical formulations.

The petroleum waxes, particularly paraffin waxes but also the microcrystalline waxes are most useful for the manufacture of candles. Petroleum waxes can be sufficiently hardened together with an intercalate and/or exfoliate, in accordance with the present invention, for candle manufacture. The petroleum waxes are predominantly long chain ($C_{16}$–$C_{50}$) alkane compounds. The paraffins are mostly straight-chain molecules, but may have branched claims, but on average have less than one branched-chain carbon atom per molecule. The microcrystalline waxes range in molecular weight from about 400 to about 700 and have average molecules of about 40 to about 50 carbon atoms. The microcrystalline waxes have more branched-chain molecules than in paraffin waxes, containing an average of three carbon atoms per side chain. Oxidized microcrystalline waxes also are useful in the compositions of the present invention. Petroleum waxes contains both solid and liquid hydrocarbons with the liquid hydrocarbons held in discrete droplets within the petroleum wax. The paraffin waxes used in the compositions of the present invention may be crude scale wax and/or fully refined wax.

Synthetic paraffin waxes are mixtures of saturated straight-chain paraffinic hydrocarbons with short side chains ($C_1$–$C_4$). The weight average molecular weight is about 700 to about 800 or about 45–60 carbon atoms per molecule.

Synthetic paraffin wax serves as an opacifier in candle formulations and is used to improve the sun-check resistance of vulcanized rubber. For use in candle formulations and in vulcanized rubber, synthetic paraffin waxes are improved in accordance with the present invention by the addition of an intercalate and/or exfoliate thereof.

The amount of intercalated and/or exfoliated layered material included in the wax compositions of the present invention may vary widely depending on the intended use of the composition. For example, relatively higher amounts of intercalates, i.e., from about 40% to about 80% by weight of the total composition, are used in forming wax compositions for increasing crack resistance and lowering shrinkage upon solidification of the wax. However, smoothening of surface finish, as well as increased crack resistance and reduced shrinkage upon solidification also can be achieved with a relatively small concentration of intercalates and/or exfoliates thereof, e.g., 0.05% to about 10% by weight. It is preferred that the intercalate or platelet loading be less than about 10% by weight of the wax composition, preferably about 0.1% to about 5% by weight of the composition. Intercalate or platelet particle loadings may vary widely, e.g., within the range of about 0.05% to about 80% by weight, preferably about 0.01% to about 20%, more preferably about 0.5% to about 10%, and most preferably about 0.1% to about 5% of the total weight of the composition. The intercalates and/or exfoliates significantly increase the resistance of cracking, lowers shrinkage upon wax solidification of the wax compositions, and improves the surface finish of the wax compositions. In most compositions, the amount of intercalate and/or platelet particles incorporated into the wax compositions is less than about 20% by weight of the total composition, and preferably from about 0.05% to about 10% by weight of the composition, more preferably from about 0.05% to about 5% by weight of the composition.

In accordance with an important feature of the present invention, the intercalate and/or platelet/wax compositions of the present invention can be manufactured in a concentrated form, e.g., as a master composition, e.g, having about 10–80%, preferably about 20–50% intercalate and/or exfoliated platelets of layered material and about 10–90%, preferably about 50–80% wax, e.g., paraffin wax. The master gel can be later diluted and mixed with additional wax and/or solvent to reduce the concentration of intercalate and/or exfoliated platelets in the composition. The intercalates, and/or exfoliates thereof, are mixed with a wax composition to produce the compositions of the present invention.

Eventual exfoliation of the intercalated layered material should provide delamination of at least about 90% by weight of the intercalated material to provide particles substantially homogeneously dispersed therein. Some intercalates require a shear rate that is greater than about 10 $sec^{-1}$ for such relatively thorough exfoliation. Other intercalates exfoliate naturally or by heating, or by applying low pressure, e.g., 0.5 to 60 atmospheres above ambient, with or without heating. The upper limit for the shear rate is not critical. In the particularly preferred embodiments of the invention, when shear is employed for exfoliation, the shear rate is from greater than about 10 $sec^{-1}$ to about 20,000 $sec^{-1}$, and in the more preferred embodiments of the invention the shear rate is from about 100 $sec^{-1}$ to about 10,000 $sec^{-1}$.

When shear is employed for exfoliation, any method which can be used to apply a shear to the intercalant/carrier composition can be used. The shearing action can be provided by any appropriate method, as for example by mechanical means, by thermal shock, by pressure alteration, or by ultrasonics, all known in the art. In particularly useful procedures, the composition is sheared by mechanical methods in which the intercalate, with or without the wax, is sheared by use of mechanical means, such as stirrers, Banbury® type mixers, Brabender® type mixers, long continuous mixers, and extruders. Another procedure employs thermal shock in which shearing is achieved by alternatively raising or lowering the temperature of the composition causing thermal expansions and resulting in internal stresses which cause the shear. In still other procedures, shear is achieved by sudden pressure changes in pressure alteration methods; by ultrasonic techniques in which cavitation or resonant vibrations which cause portions of the composition to vibrate or to be excited at different phases and thus subjected to shear. These methods of shearing are merely representative of useful methods, and any method known in the art for shearing intercalates may be used.

Mechanical shearing methods may be employed such as by extrusion, injection molding machines, Banbury® type mixers, Brabender® type mixers and the like. Shearing also can be achieved by introducing the layered material and intercalant polymer at one end of an extruder (single or double screw) and receiving the sheared material at the other end of the extruder. The temperature of the layered material/intercalant polymer composition, the length of the extruder, residence time of the composition in the extruder and the design of the extruder (single screw, twin screw, number of flights per unit length, channel depth, flight clearance, mixing zone, etc.) are several variables which control the amount of shear to be applied for exfoliation.

Exfoliation should be sufficiently thorough to provide at least about 80% by weight, preferably at least about 85% by weight, more preferably at least about 90% by weight, and most preferably at least about 95% by weight delamination of the layers to form individual platelet particles that can be substantially homogeneously dispersed in the wax composition. As formed by this process, the platelet particles dispersed in the wax composition have the thickness of the individual layers plus one to five monolayer thicknesses of complexed polymer, or small multiples less than about 10, preferably less than about 5 and more preferably less than about 3 of the layers, and still more preferably 1 or 2 layers. In the preferred embodiments of this invention, intercalation and delamination of every interlayer space is complete so that all or substantially all individual layers delaminate one from the other to form separate platelet particles for admixture with the wax composition. The compositions can include the layered material as all intercalate, completely without exfoliation, for later exfoliation during manufacture.

The effect of adding into a wax composition the nanoscale particulate dispersed platelet particles, derived from the intercalates formed in accordance with the present invention, typically is a decrease in cracking and shrinkage and an increase in stability (reduction in separation of components upon standing and solidification) of the wax composition. Other advantages include increasing the opacity and dye receptivity and an increase in wax melt viscosity for wick flame control in candles; increasing composition hardness without causing brittleness; improving the melt stability of the composition to make sure that the liquid composition remains homogenous, without component separation; reducing or eliminating the need for purer, more expensive wax components, such as microcrystalline wax; and greatly reducing or eliminating the formation of exterior bubbles or pock marks that form upon reheating an upper portion of a candle when reducing the concave upper candle end formed upon initial solidification; and providing the capability of eliminating typical opacifying agents and viscosity increasing agents, e.g. ethylene vinylacetate copolymers, fatty acids, such as stearic acid, and the like, with a much lower amount of the nanoscale platelet particles of the present invention. Additionally, the phyllosilicate platelets act as a good protector against deterioration of physical properties and color degrodation caused by ultraviolet (UV) light so that UV protectors are unnecessary in the wax compositions of the present invention.

The following specific clay:polymer complex preparations are presented to more particularly illustrate the invention and are not to be construed as limitations thereon.

Preparation of Clay—PVP Complexes (Intercalates)

Materials:

Clay—sodium montmorillonite;

PVP—molecular weights of 10,000 and 40,000.

To prepare Clay (sodium montmorillonite) - PVP complexes (intercalates) we used three different processes for polymer intercalation:

1. Mixture of the 2% PVP/water solution with the 2% clay/water suspension in a ratio sufficient to provide a polymer concentration of at least about 8% by weight, preferably at least about 10% by weight, based on the dry weight of the clay.
2. Dry clay powder (about 8% by weight moisture) was gradually added to the 2% PVP/water solution in a ratio sufficient to provide a polymer concentration of at least about 8% by weight, preferably at least about 10% by weight, based on the dry weight of the clay.
3. Dry PVP was mixed with dry clay, the mixture was hydrated with 25–50%, preferably 35%–40% by weight water, based on the dry weight of the clay, and then extruded.

Mixtures 1 and 2 were agitated at room temperature during 4 hours.

The weight ratio Clay:PVP was changed from 90:10 to 20:80.

These experiments show that all methods of preparation yielded the Clay - PVP complexes (intercalates), and the results of the intercalation do not depend on the method of preparation (1, 2, or 3) or molecular weight of the intercalant polymer (PVP), but do depend on the ratio of clay:PVP in the intercalating composition. In Table 1 the results of the X-ray diffraction for Clay - PVP complexes with different ratios of components are demonstrated. The plot of these data is shown in FIG. 1. From these data (Table 1, FIG. 1) one can see the step character of intercalation while the polymer is being sorbed in the interlayer space between adjacent platelets of the montmorillonite clay. There are increasing d(001) values from 12 Å for clay with no PVP sorbed to 24–25 Å spacing between adjacent platelets with sorption of 20–30% PVP. The next step to 30–32 Å spacing occurs when the sorbed PVP content is increased to 40–60%. Further increasing the sorbed PVP content to 70–80% increases the d(001) values to 40–42 Å. There are d(002) reflexes together with d(001) reflexes in X-ray patterns of all complexes obtained (Table 1, FIG. 1). This indicates the regularity of Clay - PVP complex structures.

TABLE 1

| | PVP, %* | d (001), Å | d (002), Å |
|---|---|---|---|
| 1 | 0.0 | 12.4 | 6.2 |
| 2 | 10.0 | 17.5 | 8.6 |
| 3 | 20.0 | 24.0 | 11.4 |
| 4 | 30.0 | 25.0 | 12.0 |
| 5 | 40.0 | 30.0 | 15.2 |
| 6 | 45.0 | 31.0 | 15.2 |
| 7 | 50.0 | 30.0 | 15.5 |
| 8 | 55.0 | 32.0 | 16.5 |
| 9 | 60.0 | 34.0 | 17.0 |
| 10 | 70.0 | 40.0 | 21.0 |
| 11 | 80.0 | 42.0 | 21.0 |

*Percent by weight, based on the dry weight of the clay plus polymer.

Preparation of Clay - PVA Complexes (Intercalates)

Materials:

Clay—sodium montmorillonite;

PVA—degree of hydrolysis 75–99%, —molecular weight of 10,000.

To prepare Clay (sodium montmorillonite) - PVA complexes (intercalates) we provided three different processes for polymer intercalation:

1. Mixture of the 2% PVA/water solution with the 2% clay/water suspension in a ratio sufficient to provide a polymer concentration of at least about 8% by weight, preferably at least about 10% by weight, based on the dry weight of the clay.
2. Dry clay powder was gradually added to the 2% PVA/water solution in a ratio sufficient to provide a polymer concentration of at least about 8% by weight, preferably at least about 10% by weight, based on the weight of the clay.
3. Dry clay was moisturized with PVA/water solution to a moisture content of 25%–80%, preferably about 35%–40% water, and then extruded.

The mixtures 1 and 2 were agitated at room temperature during 4 hours.

The weight ratio Clay:PVA was changed from 80:20 to 20:80.

Figure 2:
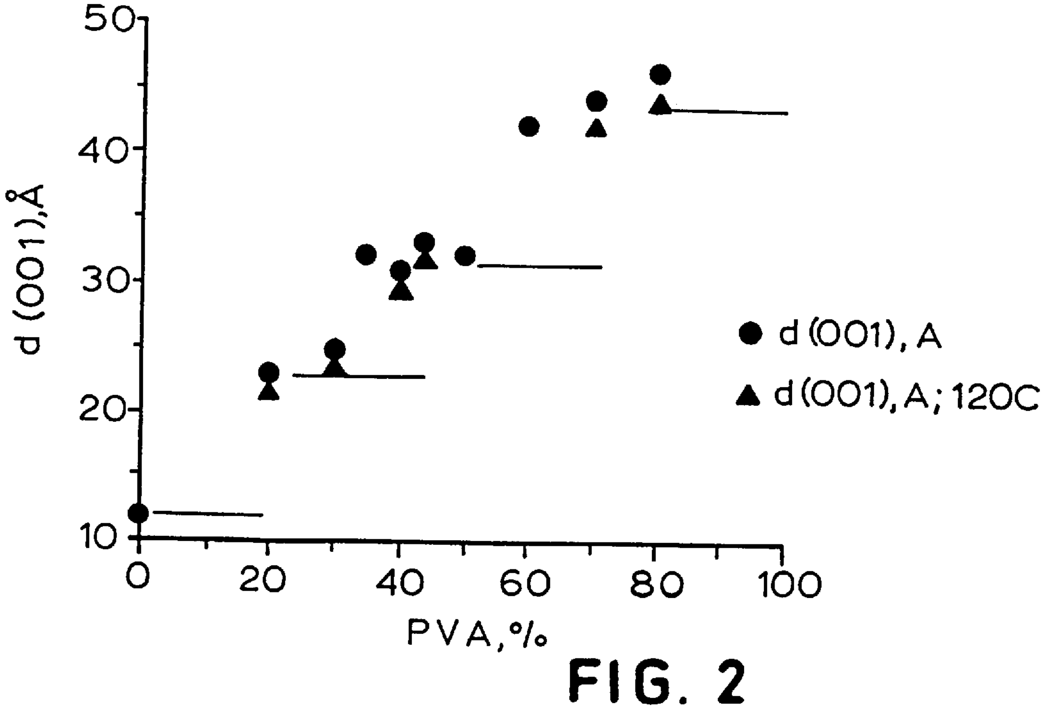
FIG. 2 is a graph plotting interlayer space for polyvinyl alcohol (PVA):smectite clay complexes (intercalates) showing d(001) spacing, in Angstroms, between smectite clay platelets versus percentage of PVA sorbed, based on the dry weight of the smectite clay.

Some of the exfoliates were studied by X-ray diffraction. These experiments show that all methods of preparation yielded the composite Clay - PVA complexes (intercalates), and the results of the intercalation do not depend on the method of preparation (1, 2, or 3), or molecular weight of the intercalant polymer (PVA), or degree of hydrolysis, but do depend on the ratio of clay:PVA in the intercalating composition. In Table 2 the results of the X-ray diffraction for Clay - PVA complexes with different ratios of components are demonstrated. The plot of these data is shown in FIG. 2. From these data (Table 2, FIG. 2) one can see the step character of increasing d(001) values from 12 Å for clay with no sorbed PVA to 22–25 Å spacing between adjacent platelets with sorption of 20–30% PVA. The next step to 30–33 Å occurs when the sorbed PVA content increases to 35–50%. A further increase of the sorbed PVA content to 60–80% increases the d(001) values to 40–45 Å.

Heating of samples at 120° C. during 4 hours insignificantly changed the d(001) values (Table 2, FIG. 2).

TABLE 2

| | PVA %* | d (001), Å | d (001), Å 120° C. |
|---|---|---|---|
| 1 | 0.0 | 12.4 | 9.6 |
| 2 | 10.0 | 17.0 | 16.8 |
| 3 | 20.0 | 23.0 | 22.0 |
| 4 | 30.0 | 25.0 | 24.0 |
| 5 | 35.0 | 32.0 | 32.0 |
| 6 | 40.0 | 31.0 | 30.0 |
| 7 | 45.0 | 33.0 | 32.0 |
| 8 | 50.0 | 32.0 | 32.0 |
| 9 | 60.0 | 42.0 | 42.0 |
| 10 | 70.0 | 44.0 | 42.0 |
| 11 | 80.0 | 45.0 | 44.0 |

*Percent by weight, based on the dry weight of the clay plus PVA.

Figure 3:
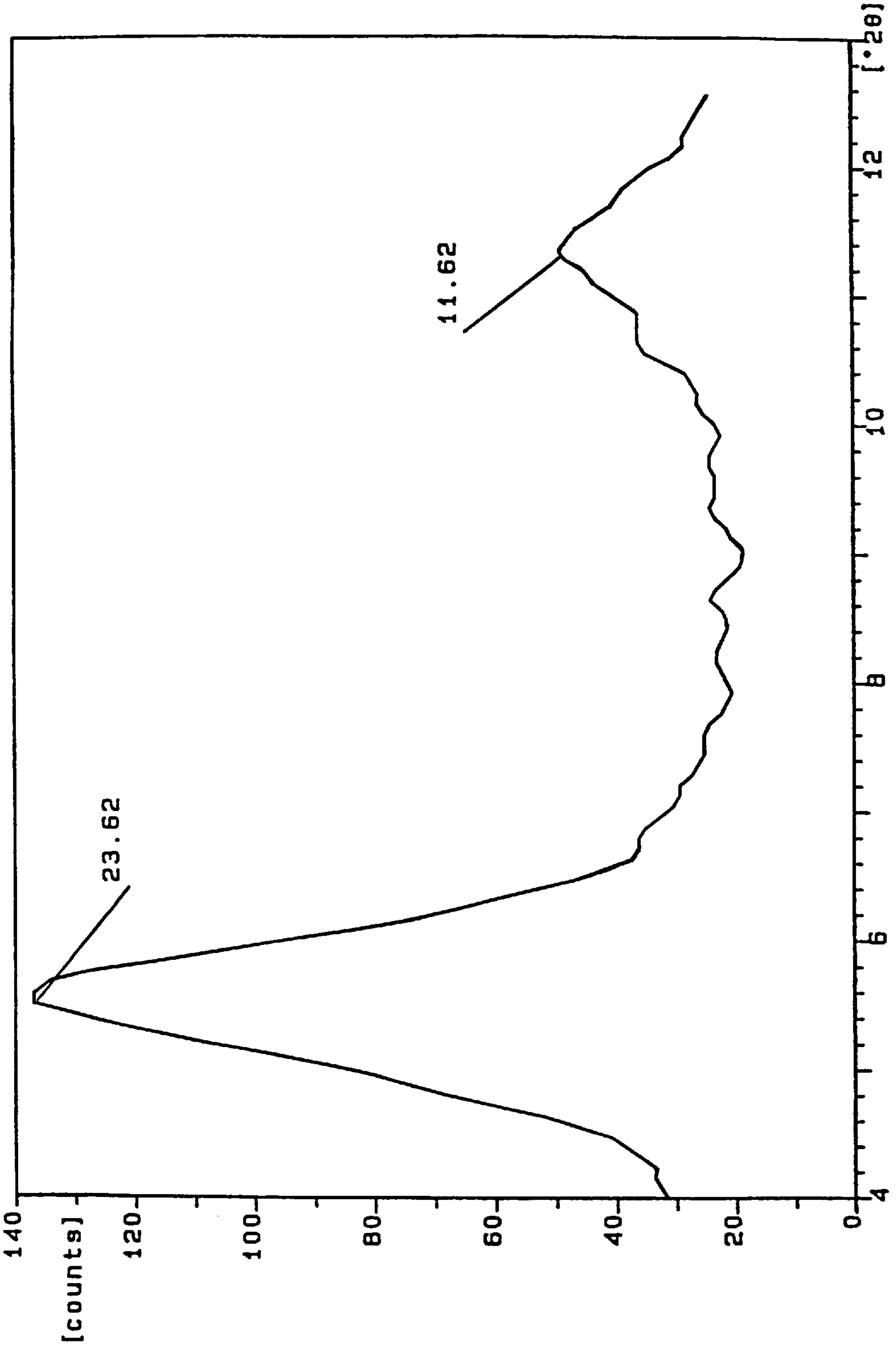
FIG. 3 is an x-ray diffraction pattern for a complex of PVP (weight average molecular weight of 10,000):sodium montmorillonite clay, in Angstroms, at a weight ratio of PVP:clay of 20:80.
Figure 4:
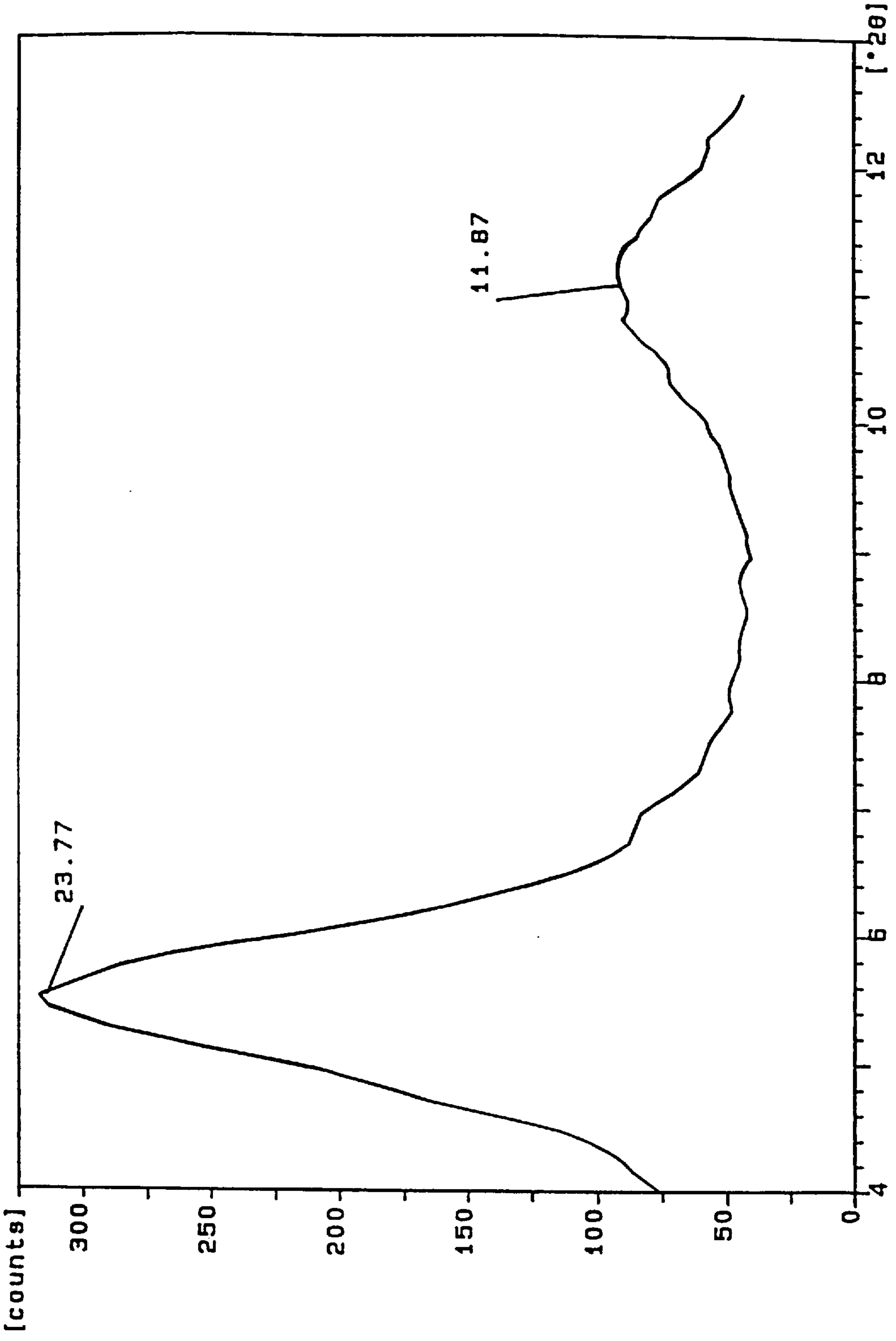
FIG. 4 is an x-ray diffraction pattern for a complex of PVP (weight average molecular weight of 40,000):sodium montmorillonite clay, in Angstroms, at a weight ratio of PVP:clay of 20:80.
Figure 5:
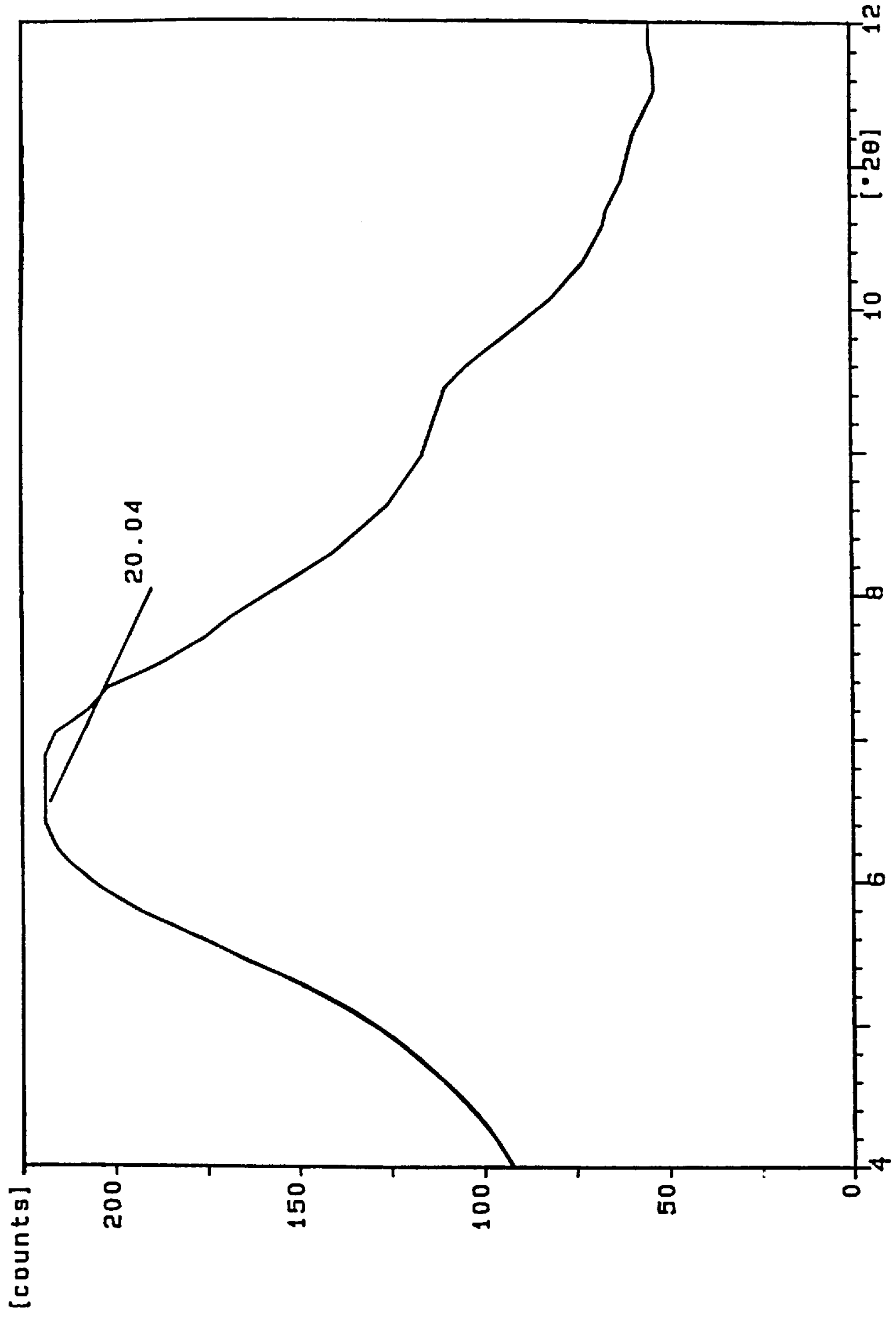
FIG. 5 is an x-ray diffraction pattern for a complex of PVA (weight average molecular weight of 15,000):sodium montmorillonite clay, in Angstroms, at a weight ratio of PVA:clay of 20:80.
Figure 6:
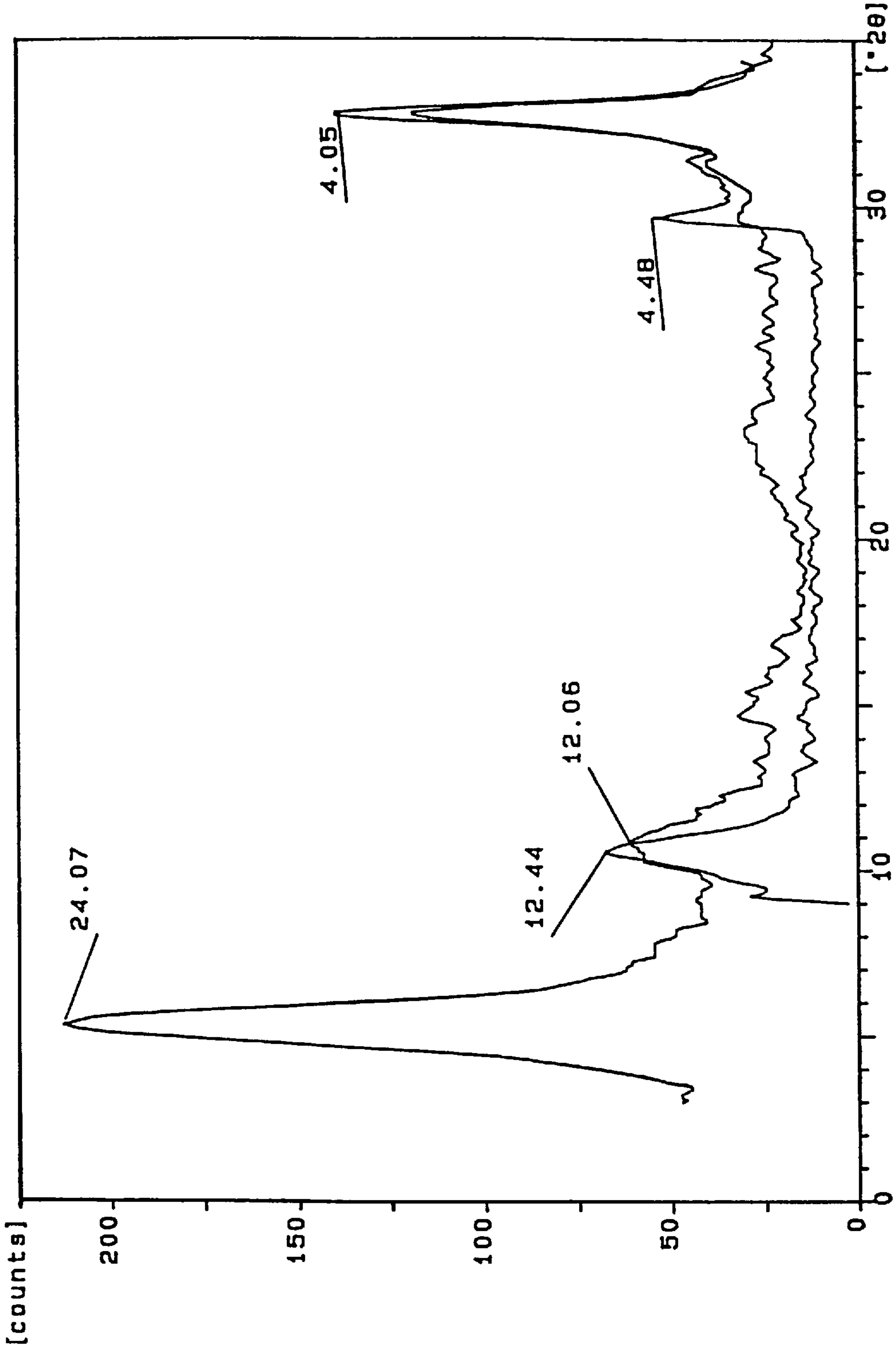
FIG. 6 is an x-ray diffraction pattern for a complex of PVP:sodium montmorillonite clay, in Angstroms, at a weight ratio of PVP:clay of 20:80 (upper pattern); and an-x-ray diffraction pattern for ≈100% sodium montmorillonite clay having a crystobalite impurity (lower pattern)
Figure 7:
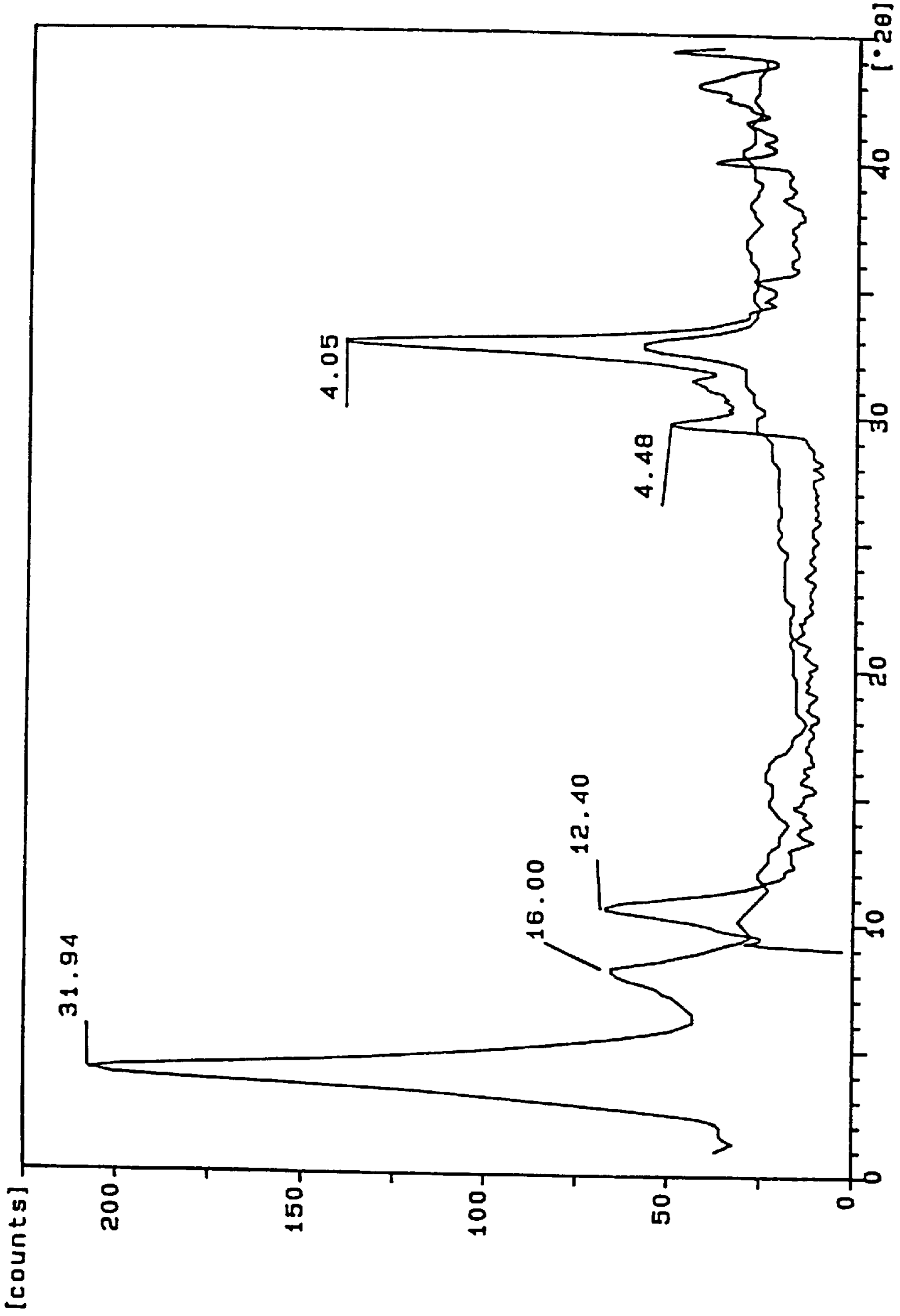
FIG. 7 is an x-ray diffraction pattern for a complex of PVP:sodium montmorillonite clay, in Angstroms, at a weight ratio of PVP:clay of 50:50 (upper pattern); and an x-ray diffraction pattern for ≈100% sodium montmorillonite clay having a crystobalite impurity (lower pattern)

The graphs of FIGS. 3 to 5 are x-ray diffraction patterns of blends of different water-soluble polymers with sodium bentonite clay. The pattern of FIGS. 3 and 4 are taken from intercalated clay 20% by weight polyvinylpyrrolidone (weight average molecular weight=10,000 for FIG. 3; 40,000 for FIG. 4) and 80% by weight sodium bentonite clay. The blends were formed by mixing the PVP and clay from a 2% solution of PVP and a 2% dispersion of sodium bentonite in a 1:4 ratio, respectively. As shown, the PVP-:clay complexed since no d(001) smectite peak appears at about 12.4 Å. Similar results are shown for 20% polyvinyl alcohol, 80% sodium bentonite, as shown in FIG. 5, blended in the same way and in the same ratio. The d(001) peak of non-exfoliated (layered) sodium bentonite clay appears at about 12.4 Å, as shown in the x-ray diffraction pattern for sodium bentonite clay (containing about 10% by weight water) in the lower x-ray diffraction patterns of FIGS. 6 and 7. The graphs of FIG. 6 are x-ray diffraction patterns of sodium bentonite clay (montmorillonite) and a PVP:clay complex that was obtained by extrusion of a blend of 20% by weight polyvinylpyrrolidone (molecular weight 10,000) and 80% by weight sodium bentonite clay (containing a crystobalite impurity, having a d-spacing of about 4.05 Å) with 35% water based on the weight of dry clay plus polymer. As shown in FIG. 6, the PVP clay complexed since no d(001) smectite peak appears at about 12.4 Å. There are basil spacings with a d(001) peak of PVP:clay complex at about 24 Å and d(002) peak of PVP:clay complex at about 12 Å, that shows close to regular structure of this intercalated composite with a PVP:clay ratio equal to 1:4. The graphs of FIG. 7 are x-ray diffraction patterns of sodium bentonite clay (montmorillonite) and PVP:clay complex that was obtained by extrusion of blend of 50% by weight polyvinylpyrrolidone (molecular weight 10,000) and 50% of sodium bentonite clay (containing a crystobalite impurity, having d-spacing of about 4.05 Å) with 35% water based on the weight of dry clay plus polymer. As shown in FIG. 7, the PVP:clay complexed since no d(001) smectite peak appears at about 12.4 Å. There are basil spacings with a d(001) peak of the PVP:clay complex at about 32 Å and a d(002) peak of PVP:clay complex at about 16 Å that shows close to regular structure of this intercalated composite with a PVP-:clay ratio equal to 1:1. When mechanical blends of powdered sodium bentonite clay (containing about 10% by weight water) and powdered polyvinylpyrrolidone (PVP) polymer were mixed with water (about 75% by weight water), the polymer was intercalated between the bentonite clay platelets, and an exothermic reaction occurred that, it is theorized, resulted from the polymer being bonded to the internal faces of the clay platelets sufficiently for exfoliation of the intercalated clay.

It should be noted, also, that exfoliation did not occur unless the bentonite clay included water in an amount of at least about 4% by weight, based on the dry weight of the clay, preferably at least about 10% by weight water. The water can be included in the clay as received, or can be added to the clay prior to or during intercalant polymer contact.

It should also be noted that the exfoliation occurred without shearing—the layered clay exfoliated naturally after sufficient intercalation of polymer between the platelets of the layered bentonite—whether the intercalate was achieved by using sufficient water, e.g., at least about 20% by weight, preferably about 30% to about 100% by weight, or higher, based on the dry weight of the clay, for sufficient migration of the polymer into the interlayer spaces, and preferably also by extruding. When intercalating in a phyllosilicate slurry, it has been found that at least about 65% by weight water, based on the total weight of the intercalating composition, provides easier mixing and faster migration of the polymer into the spaces between platelets.

Figure 8:
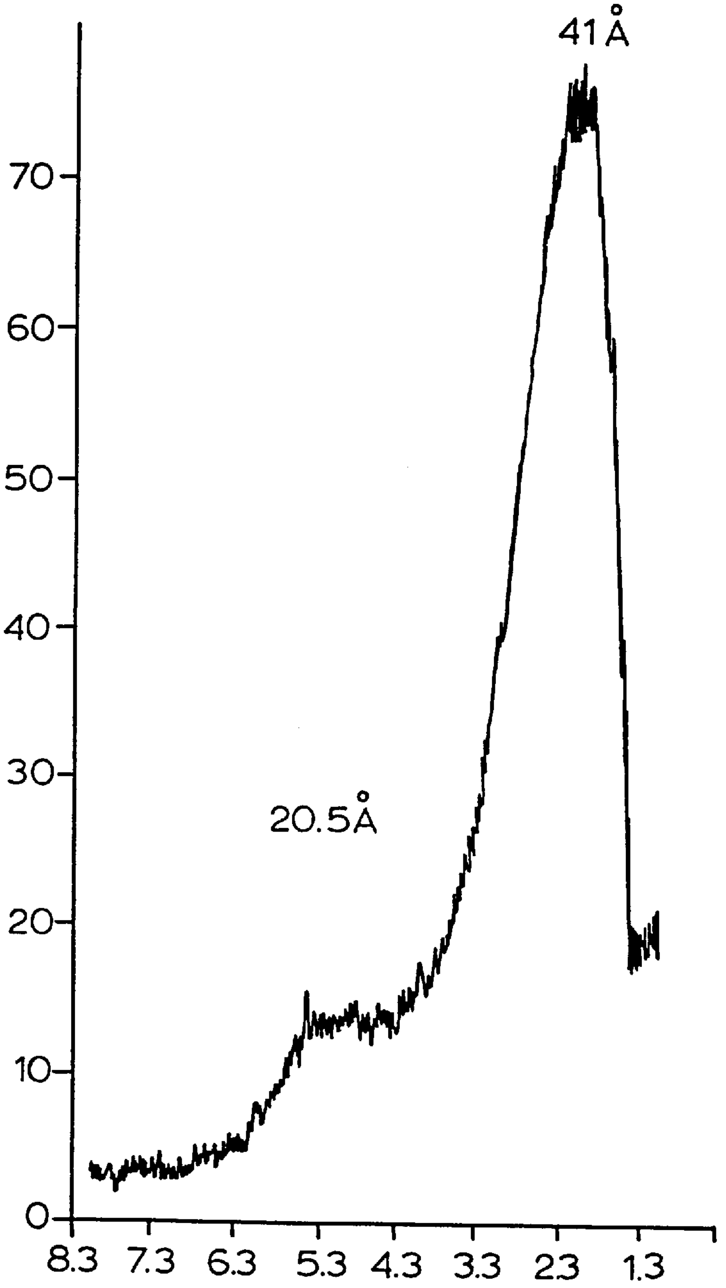
FIG. 8 is a portion of an x-ray diffraction pattern for PVP:sodium montmorillonite clay, in Angstroms, at a PVP-:clay ratio of 80:20, showing a PVP:clay complex peak or d(001) spacing of about 41 Å.

The x-ray diffraction pattern of FIG. 8 shows that at a ratio of 80% PVP, 20% clay, the periodicity of the intercalated composite, with a PVP clay ratio equal to 4:1, is increased to about 41 Å.

EXAMPLE

A candle composition is prepared as follows:

| Component | Weight % |
|---|---|
| petroleum-derived paraffin wax | 94 |
| microcrystalline wax | 3 |
| sodium bentonite platelets exfoliated from a PVP intercalate | 3 |

The candle composition is solidified into a candle form and exhibits excellent stability (without separation of the platelets from the composition); excellent hardness without brittleness; significantly less shrinkage, without cracking; and the melt has ideal viscosity for good flow and flame control.

What is claimed is:

1. A composition consisting essentially of exfoliated platelets of a layered material formed from an intercalate, together with a wax composition, said intercalate formed by contacting a layered material, having a moisture content of at least about 4% by weight, with an intercalant polymer to form an intercalating composition containing at least about 16% by weight intercalant polymer based on the dry weight of the layered material, said intercalate having a weight ratio of polymer to layered material of about 16–90 grams of polymer per 100 grams of dry layered material to achieve sorption and complexing of the polymer between adjacent spaced layers of the layered silicate material, without prior sorption of an onium ion or silane coupling agent, to expand the spacing between a predominance of the adjacent platelets of said layered silicate material to at least about 5 Å, when measured after sorption of the intercalant polymer and drying to a maximum of 5% by weight water, and delaminating at least about 80% of the intercalated material into platelet particles having less than five platelet layers.

2. A composition in accordance with claim 1, wherein the concentration of intercalant polymer in said intercalating composition is at least about 0.1% by weight, based on the weight of water and polymer in the intercalating composition.

3. A composition in accordance with claim 2, wherein the concentration of intercalant polymer in said intercalating composition is at least about 1% by weight.

4. A composition in accordance with claim 3, wherein the concentration of intercalant polymer in said intercalating composition is at least about 2% by weight.

5. A composition in accordance with claim 1, wherein the concentration of intercalant polymer in said intercalating composition is in the range of about 10%–60% by weight.

6. A composition in accordance with claim 4, wherein the concentration of intercalant polymer in said intercalating composition is at least about 15% by weight, based on the dry weight of layered material in the intercalating composition, to achieve spacing of said adjacent platelets of at least about 10 Å.

7. A composition in accordance with claim 6, wherein the concentration of intercalant polymer in said intercalating composition is at least about 20% by weight, based on the dry weight of layered material in the intercalating composition, and wherein said intercalant polymer includes a functionality selected from the group consisting of an aromatic ring, a carboxyl, a hydroxyl, a carbonyl, an ether, an ester, an amine, an amide, an SOx, a POx, wherein x=2,3 or 4, and mixtures thereof.

8. A composition in accordance with claim 7, wherein the concentration of intercalant polymer in said intercalating composition is at least about 30% by weight, based on the dry weight of layered material in the intercalating composition.

9. A composition in accordance with claim 1, wherein the concentration of intercalant polymer in said intercalating composition in the range of about 50% to about 90% by weight, based on the weight of polymer plus water.

10. A composition in accordance with claim 9, wherein the concentration of intercalant polymer in said intercalating composition is in the range of about 50% to about 80% by weight.

11. A composition in accordance with claim 1, wherein the concentration of intercalant polymer in the intercalating composition is at least about 16% by weight, based on the dry weight of the layered material.

12. A composition in accordance with claim 11, wherein the concentration of intercalant polymer in the intercalating composition is in the range of about 16% to about 70% by weight, based on the dry weight of the layered material.

13. A composition in accordance with claim 1, wherein the weight ratio of intercalant polymer to layered material in the intercalating composition is in the range of about 1:20 to about 10:1.

14. A composition in accordance with claim 11, wherein the weight ratio of intercalant polymer to layered material is at least 1:12.

15. A composition in accordance with claim 14, wherein the weight ratio of intercalant polymer to layered material in the intercalating composition is at least 1:5.

16. A composition in accordance with claim 15, wherein the weight ratio of intercalant polymer to layered material in the intercalating composition is in the range of 1:5 to 1:3.

17. A composition in accordance with claim 1, wherein the intercalant polymer is selected from the group consisting of polyvinylpyrrolidone; polyvinyl alcohol; polyvinylimine; and mixtures thereof.

18. A composition in accordance with claim 17, wherein the intercalant polymer is polyvinyl alcohol.

19. A composition in accordance with claim 13, wherein the intercalant polymer is polyvinylpyrrolidone.

20. A composition in accordance with claim 18, wherein the intercalant polymer is polyvinyl alcohol having less than about 5% by weight acetal substituents in the polymer.

21. A composition in accordance with claim 17, wherein the intercalant polymer has a weight average molecular weight in the range of about 100 to about 100,000.

22. A composition in accordance with claim 17, wherein the intercalant polymer has a weight average molecular weight in the range of about 200 to about 40,000.

23. A composition in accordance with claim 22, wherein the intercalant polymer is polyvinylpyrrolidone.

24. A composition in accordance with claim 22, wherein the intercalant polymer is a polyvinyl alcohol.

25. A composition in accordance with claim 1, wherein the intercalant polymer is a homopolymer or copolymer of N-vinylpyrrolidone.

26. A method of decreasing the shrinkage and increasing the crack resistance of a wax composition comprising combining said wax composition with an intercalate complex of a phyllosilicate and polymer to form a composition consisting essentially of said wax composition and said intercalate complex comprising:

contacting the phyllosilicate, having a water content of at least about 4% by weight, with an intercalant polymer to form an intercalating composition having at least about 16% by weight intercalant polymer based on the dry weight of the phyllosilicate, to form an intercalate having a weight ratio of polymer to phyllosilicate in the range of about 16–90 grams of polymer per 100 grams of dry phyllosilicate, wherein intercalation of said polymer between said adjacent phyllosilicate platelets of said intercalate is achieved without prior sorption of an onium ion or silane coupling agent and sufficient to space said adjacent phyllosilicate platelets a distance of at least about 5 Å;

exfoliating said intercalate; and combining said exfoliate with a material consisting essentially of said wax composition.

27. The method of claim 26, wherein said intercalating composition includes a water intercalating carrier comprising about 4% to about 5000% by weight water, capable of dissolving said polymer, based on the dry weight of said phyllosilicate.

28. The method of claim 27, wherein said intercalating composition includes water in an amount of about 30% to about 40% by weight.

29. The method of claim 28, wherein said water content of said intercalating composition comprises about 35% to about 40% by weight, based on the dry weight of said phyllosilicate.

30. The method of claim 27, wherein said intercalating composition comprises about 5% to about 50% by weight water, based on the dry weight of said phyllosilicate.

31. The method of claim 27, wherein said intercalating composition includes water in an amount of about 7% to about 100% by weight, based on the dry weight of the phyllosilicate in the intercalating composition.

32. A composition consisting essentially of a wax having about 16 to about 60 carbon atoms per molecule, in an amount of about 0.5% to about 99.95% by weight of the composition, and about 0.05% to about 80% by weight of the composition of an exfoliate of a phyllosilicate material, said exfoliate formed by contacting a phyllosilicate, having a water content of at least about 4% by weight, with an intercalant polymer in an amount of at least about 16% by weight intercalant polymer based on the dry weight of the phyllosilicate to form an intercalate having said intercalant polymer sorbed between adjacent spaced layers of the phyllosilicate and complexed on platelet surfaces of said phyllosilicate in an amount of about 16–90 grams of intercalant polymer per 100 grams of dry phyllosilicate material, without prior sorption of an onium ion or silane coupling agent, to expand the spacing between a predominance of the adjacent phyllosilicate platelets to at least about 5 Å, when measured after sorption of the polymer and drying of the intercalate to a maximum water content of 5% by weight, and exfoliating at least about 80% of the intercalated material into platelet particles having less than five platelet layers.

33. The composition of claim 32, wherein the wax has about 18 to about 50 carbon atoms, and mixtures thereof.

34. A composition in accordance with claim 32, wherein the intercalant composition has a weight ratio of intercalant polymer to phyllosilicate of at least about 1:20.

35. A composition in accordance with claim 34, wherein the weight ratio of intercalant polymer to phyllosilicate in said intercalating composition is at least about 1:12.

36. A composition in accordance with claim 35, wherein the weight ratio of intercalant polymer to phyllosilicate in said intercalating composition is at least about 1:10.

37. A composition in accordance with claim 36, wherein the weight ratio of intercalant polymer to phyllosilicate in said intercalating composition is at least about 1:5.

38. A composition in accordance with claim 37, wherein the weight ratio of intercalant polymer to phyllosilicate in said intercalating composition in the range of about 1:5 to about 9:1.

39. A composition in accordance with claim 38, wherein the weight ratio of intercalant polymer to phyllosilicate in said intercalating composition in the range of about 1:5 to about 1:3.

40. A composition in accordance with claim 34, wherein the concentration of intercalant polymer in the intercalating composition is at least about 16% by weight, based on the dry weight of the phyllosilicate.

41. A composition in accordance with claim 40, wherein the concentration of intercalant polymer in the intercalating composition is in the range of about 16% to about 70% by weight, based on the dry weight of the phyllosilicate.

42. A composition in accordance with claim 40, wherein the concentration of intercalant polymer in the intercalating composition is in the range of about 16% to less than about 35% by weight, based on the dry weight of the phyllosilicate.

43. A composition in accordance with claim 41, wherein the concentration of intercalant polymer in the intercalating composition is in the range of about 35% to less than about 55% by weight, based on the dry weight of the phyllosilicate.

44. A composition in accordance with claim 41, wherein the concentration of the intercalant polymer in the intercalating composition is in the range of about 55% to less than about 70% by weight, based on the dry weight of the phyllosilicate.

45. A composition in accordance with claim 32, wherein the wax has about 16 to about 40 carbon atoms per molecule.

46. A method of manufacturing a wax composition consisting essentially of about 20% to about 99.95% by weight of a wax and about 0.05% to about 80% by weight of exfoliated platelets of an intercalated layered material, said intercalated layered material having a water-soluble polymer intercalated between and bonded to said platelet surfaces thereof through a bonding mechanism selected from the group consisting of ionic complexing; electrostatic complexing; chelation; hydrogen bonding; dipole/dipole; Van Der Waals forces; and any combination thereof, comprising:

contacting the layered material with a water-soluble intercalant polymer and water, without prior sorption of an onium ion or silane coupling agent, to form an intercalating composition having at least about 16% by weight intercalant polymer based on the dry weight of the phyllosilicate to form an intercalate having said polymer intercalated between said adjacent platelets in an amount of about 16–90 grams of polymer per 100 grams of dry phyllosilicate;

combining the intercalate with said wax; and exfoliating the spaced platelets of said intercalate into at least about 80% by weight of platelet particles having less than three individual platelets.

47. The method of claim 46, wherein said layered material is a phyllosilicate and said intercalating composition is an aqueous solution comprising about 4% to about 5000% by weight water, based on the dry weight of said phyllosilicate in said intercalating composition.

48. The method of claim 47, wherein said intercalating composition comprises about 30% to about 50% water, based on the dry weight of the phyllosilicate.

49. The method of claim 48, wherein said intercalating composition comprises about 35% to about 45% by weight water.

50. A method of manufacturing a candle comprising wax and a phyllosilicate intercalate comprising:

contacting the phyllosilicate with an intercalating composition comprising the phyllosilicate, an intercalant polymer, and water, wherein the weight ratio of the intercalant polymer to phyllosilicate is at least 1 to about 20, and the concentration of said water-soluble intercalant polymer is at least about 5% up to about 900% polymer, based on the dry weight of the phyllosilicate, to form an intercalate having said intercalant polymer intercalated between said adjacent phyllosilicate platelets in an amount sufficient to space said adjacent phyllosilicate platelets to a distance of at least about 5 Å; and combining the intercalate with said wax and a wick held within said wax.

* * * * *